(12) United States Patent
Nistor

(10) Patent No.: US 8,569,061 B2
(45) Date of Patent: *Oct. 29, 2013

(54) STEM CELL GROWTH MEDIA AND METHODS OF MAKING AND USING SAME

(75) Inventor: Gabriel Nistor, Placentia, CA (US)

(73) Assignee: California Stem Cell, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/151,163

(22) Filed: Jun. 1, 2011

(65) Prior Publication Data

US 2011/0306129 A1    Dec. 15, 2011

Related U.S. Application Data

(63) Continuation of application No. 11/969,120, filed on Jan. 3, 2008, now Pat. No. 7,977,096.

(60) Provisional application No. 60/883,281, filed on Jan. 3, 2007.

(51) Int. Cl.
*C12N 5/00* (2006.01)
*C12N 5/02* (2006.01)
*C12N 5/071* (2010.01)

(52) U.S. Cl.
USPC .......................... 435/377; 735/366; 735/384

(58) Field of Classification Search
USPC ........................................ 435/377, 366, 384
See application file for complete search history.

(56) References Cited

U.S. PATENT DOCUMENTS 7,977,096 B2 *    7/2011    Nistor .......................... 435/405

OTHER PUBLICATIONS

Ludwig et al. Nat. Biotech., 24(2): 185-187, 2006.*
Xu et al. Nature Biotech.;19: 971-974, 2001.*
Amit et al. Biol. of Reprod., 70: 837-845, 2004.*
Ludwig et al., Nature Biotechnology24(2): 185-187; Supplemental Table S1 and Supplemental Methods only, 2006.*

* cited by examiner

*Primary Examiner* — Thaian N Ton
(74) *Attorney, Agent, or Firm* — Baker & Hostetler LLP; Mark Krietzman

(57) ABSTRACT

The invention provides media formulations. A complete media formulation of the invention includes, for example, the following components: albumin, an iron carrier, glutamine, a glycosidase or hydrolase, fibroblast growth factor (FGF), a salt or mineral, and essential amino acids at an osmolarity of about 220-330 mOsm/Liter.

10 Claims, 15 Drawing Sheets

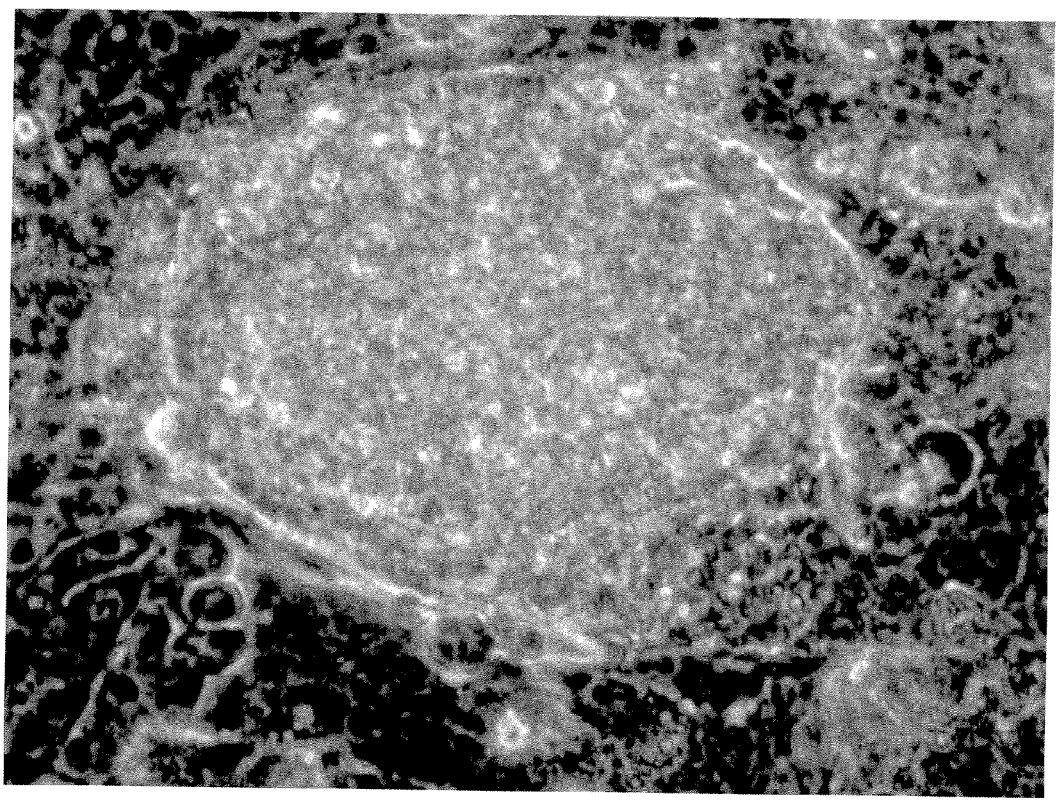
Fig, 3D

STEM CELL GROWTH MEDIA AND METHODS OF MAKING AND USING SAME

STATEMENT OF PRIORITY AND RELATED APPLICATIONS

This application is a continuation of U.S. Utility patent application Ser. No. 11/969,120, filed Jan. 3, 2008 now U.S. Pat. No. 7,977,096, which claims priority to U.S. Application Ser. No. 60/883,281, filed on Jan. 3, 2007, which is expressly incorporated herein by reference as if fully set forth herein.

INTRODUCTION

The typical conditions for the growth of the cells such as stem cells involve a base media (DMEM or DMEM:FI2) supplemented with serum or serum replacement. Stem cell colonies are grown on mouse embryonic fibroblasts (or fibroblasts from other species, including humans) mitotically inactivated by treatment with a cytostatic or by irradiation. Alternatively, growth media can be exposed to supportive cultures, collected, sterile filtered and used to fECd the stem cell cultures. Typically the media is supplemented with basic FGF. As a result of exposure to non-human tissue, stem cells or their derivatives cultured as above cannot be used in clinical, human applications, due to the possibility of xeno-contamination.

Other groups have reported growth of stem cells using serum frEC media supplemented with B27 (Invitrogen) and large amounts of bFGF (40-100 ng/ml), or using high density cultures in the absence of supportive cells. A mixture of growth factors including neurotrophins has also bECn tested with relative success. When low amounts of growth factors were used in serum frEC media, a spontaneous differentiation tendency towards ectodermal lineage was observed. Mixtures or high concentrations of growth factors led to increased incidences of chromosomal abnormalities.

Hyaluronic acid (HA) is a nonsulfated linear glycosaminoglycan (GAG), one of the principal extra cellular matrix components in nearly all tissues involved in the regulation of cell proliferation, adhesion and migration. Additional GAGs of physiological significance are hyaluronic acid, dermatan sulfate, chondroitin sulfate, heparin, heparan sulfate, and keratin sulfate. Each of these GAGs has a predominant disaccharide. Hyaluronic acid is unique among the GAGs in that it does not contain any sulfate and is not found covalently attached to proteins as a proteoglycan. It is, however, a component of non-covalently formed complexes with proteoglycans in the extra-cellular matrix. Hyaluronic acid polymers are very large (with molecular weights of 100,000-10,000,000) and can displace a large volume of water.

SUMMARY

The invention provides media formulations. Media formulations may be sterile or non-sterile. In one embodiment, a complete media formulation includes: albumin, an iron carrier, glutamine, a glycosidase or hydrolase, fibroblast growth factor (FGF), a salt or mineral, and essential amino acids, at an osmolarity of about 220-330 mOsm/Liter. In another embodiment, a complete media formulation includes: albumin, an iron carrier, glutamine, a glycosaminoglycan degradation product, fibroblast growth factor (FGF), a salt or mineral, and essential amino acids, at an osmolarity of about 220-330 mOsm/Liter.

Complete and incomplete media formulations include formulations with components (ingredients) in amounts compatible with survival or proliferation of cells. Exemplary cells include mammalian cells, such as embryonic, tissue specific, germinal and adult stem cells. Stem cells include multipotent, totipotent and pluripotent stem cells. In particular aspects, components are in amounts compatible with survival or proliferation of stem cells without substantial differentiation.

Albumin is a particular example of a component of a media formulation of the invention. A non-limiting amount of albumin, is a concentration of about 5 to 100 grams/Liter.

An iron carrier is a particular example of a component of a media formulation of the invention. Iron carriers include transferrin. A non-limiting amount of transferrin, is a concentration of about 5 to 100 ug/ml.

Glutamine is a particular example of a component of a media formulation of the invention. Glutamine can be provided as a peptide, such as a di-, tri-, tetra-, etc.-peptide. A non-limiting example of a di-peptide is glutamine-alanine. A non-limiting amount of glutamine, is a concentration of about 10 to 40 mg/Liter.

A glycosidase or hydrolase is a particular example of a component of a media formulation of the invention. A particular non-limiting example is a hyaluronidase (e.g., hyaluronidase type 1). Additional particular non-limiting examples are a glycosidase or hydrolase enzyme set forth in Table 1. A non-limiting amount of a glycosidase or hydrolase, is a concentration of about 1 to 100 ug/ml.

A fibroblast growth factor (FGF) is a particular example of a component of a media formulation of the invention. Particular non-limiting examples are basic FGF and acidic FGF. Additional particular non-limiting examples are FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. A non-limiting amount of an FGF, is a concentration of about 5 to 100 ng/ml. FGF can optionally be produced or provided by feeder cells.

A salt or mineral is a particular example of a component of a media formulation of the invention. Particular non-limiting examples are sodium, potassium, calcium, magnesium, copper, manganese, molybdenum, selenium (e.g., sodium selenite), iron, and zinc. A non-limiting amount of sodium, is a concentration of 130-160 mg/Liter. A non-limiting amount of potassium, is a concentration of 3 to 6 mg/Liter. A non-limiting amount of calcium, is a concentration of 7 to 12 mg/Liter. A non-limiting amount of magnesium, is a concentration of 1 to 4 mg/deciliter. Non-limiting amounts of copper, manganese, molybdenum, selenium, iron, and zinc, is a concentration of 1 pg/deciliter to 1 ug/deciliter.

One or more essential amino acids is a particular example of a component of a media formulation of the invention. Particular examples are arginine, cystine, histidine, isoleucine, leucine, methionine, phenylalanine, threonine, tryptophan, tyrosine and valine. A non-limiting amount of an essential amino acid, is a concentration of about 0.5 to 10 nmol/Liter. An additional non-limiting amount of an essential amino acid, is a concentration of about 2.5 nmol/Liter.

Media formulations include formulations having desired or target osmolarities, for example, when the media comprises a liquid. A non-limiting osmolarity is about 240-300 mOsm/Liter. An additional non-limiting osmolarity is about 250-270 mOsm/Liter.

A globulin is a particular example of a component of a media formulation of the invention. Particular non-limiting examples of globulins include alpha, beta and gamma globulins. An additional non-limiting example of a globulin is an antibody (e.g., IgG, IgA, IgM, IgE and IgD). A non-limiting amount of globulin, is a concentration of about 0.1 to 20 grams/Liter. An additional non-limiting amount of globulin, is a relative ratio of globulin to albumin of about 1:2, or less than 1:2.

Media formulations include formulations that are pH buffered. Particular non-limiting examples of buffering agents are bicarbonates, phosphates, ethanolamines, triethanolamines and trometamols. Particular non-limiting examples of pH, are ranges between about 6.8-7.8 when present in a 2-20% oxygen environment, in a 5-15% carbon dioxide environment, or in a 0.04-0.06% carbon dioxide and 20-21% oxygen environment.

One or more energy sources is a particular example of a component of a media formulation of the invention. Particular examples are a mono-saccharide (e.g., glucose) or poly-saccharide. A non-limiting amount of glucose, is a concentration of about 10 to 1000 mg/Liter. An additional non-limiting example of an energy source is pyruvate.

Additional components of a media formulation of the invention include, for example, one or more of a non-essential amino acid, a hormone, a growth factor, vitamin, heparin, heparin sulfate or a glycosaminoglycan degradation product. Particular examples of non-essential amino acids are alanine, asparagine, aspartate, glutamine, glycine, proline and serine. Particular examples of hormones are insulin, insulin-like growth factor, a thyroid hormone (e.g., thyroxine (T4) and triiodothyronine (T3)), and a progesterone. A non-limiting amount of insulin or insulin-like growth factor, is a concentration between about 5 to 40 ug/ml. A non-limiting amount of thyroid hormone, is a concentration between about 5 to 40 ng/ml. Particular examples of glycosaminoglycan degradation products include a hyaluronic acid degradation product. Glycosaminoglycan degradation products can one or more of di-, tri-, tetra-, penta-, hexa-, hepta-, octa-saccharide, or larger saccharide polymers.

Additional components of a media formulation of the invention include, for example, a substrate. A non-limiting example of a substrate is an adhesion molecule. Adhesion molecules include, for example, laminin, fibronectin, or a proteoglycan (e.g., hyaluronic acid, chondroitin, chondroitin sulfate or a mucin). Adhesion molecules such as proteoglycans can be produced or provided by feeder cells.

An anti-microbial is a particular example of a component of a media formulation of the invention. Particular non-limiting examples of anti-microbials include anti-bacterials, anti-virals, anti-mycoplasmas or anti-fungals.

Complete and incomplete media formulations include dry and liquid formulations. Volumes of media can be convenient for handling or for shipment. A non-limiting example of a liquid media, is a volume of about 100-250 ml, 250-500 ml, or 500-1000 ml.

The invention provides kits and containers that include media formulations, either sterile or non-sterile. Kits and containers include, for example, packaging material suitable for liquid or dry complete or incomplete media formulations (e.g., suitable for a volume of media of about 100-250 ml, 250-500 ml, or 500-1000 ml). Kits also include, for example, labels, as well as instructions, for example, instructions for maintaining survival or proliferation of cells (e.g., stem cells).

Kits and containers can include a plurality of complete or incomplete media formulations. A particular non-limiting example of a kit includes first and second containers, in which the first container has a media formulation with the following components: an iron carrier, a salt or mineral, and essential amino acids; and the second container has following components: albumin, glutamine, a glycosidase or hydrolase, and fibroblast growth factor (FGF). Kits and containers include media formulations that, when combined, provide a complete media formulation. Kits and containers include media formulations that, when combined, produce a complete media formulation having a desired or target osmolarity, for example, an osmolarity of about 220-330 mOsm/Liter.

The invention provides methods of producing media formulations. In one embodiment, a complete media formulation is produced by combining albumin, an iron carrier, glutamine, a glycosidase or hydrolase, fibroblast growth factor (FGF), a salt or mineral, and essential amino acids. In another embodiment, a complete media formulation is produced by combining albumin, an iron carrier, glutamine, a glycosaminoglycan degradation product, fibroblast growth factor (FGF), a salt or mineral, and essential amino acids. Such complete media formulations, when combined, have a desired or target osmolarity, for example, in a non-limiting example, the media formulation is a liquid that has an osmolarity of about 220-330 mOsm/Liter.

The invention provides cell cultures that include a complete media formulation of the invention. Non-limiting examples of cell cultures include mammalian cells, for example, mammalian primary, secondary or passaged cells, and immortalized cells. Additional non-limiting examples of cell cultures include mammalian stem cells, for example, embryonic, tissue specific, germinal and adult stem cells. Further non-limiting examples of cell cultures include mammalian multipotent, totipotent and pluripotent stem cells. Cell cultures of the invention include other cells, such as feeder cells (e.g., FGF or proteoglycan producing feeder cells).

The invention provides methods for culturing cells, including mammalian cells such as mammalian primary, secondary or passaged cells, and immortalized cells; embryonic, tissue specific, germinal and adult, multipotent, totipotent and pluripotent stem cells. In one embodiment, a method includes growing or incubating cells in a complete media formulation of the invention for a period of time allowing cells to proliferate, for example, increase in numbers by 25%, 50%, 75%, 100% or more. In another embodiment, a method includes growing or incubating cells in a complete media formulation of the invention for at least about 30, 60, 90, 120, 240 minutes or more. In an additional embodiment, a method includes growing or incubating cells in a complete media formulation of the invention for at least about 1, 2, 3, 4, 5, 6, 7, 8, 10, 12, 16, 20, 24, 36, or 48 hours or more. In a further embodiment, a method includes growing or incubating stem cells in a complete media formulation of the invention under conditions in which stem cells survive or proliferate without substantial differentiation. Methods for culturing cells include maintaining pluripotency of stem cells, or a majority of stem cells in the culture (e.g., 50%, 60%, 70%, 80% or more remain pluripotent), for a plurality of passages, e.g., 2, 3, 4, 5 or more passages. Methods for culturing cells also include co-cultures, for example, culturing the cells with other cells, such as feeder cells (e.g., FGF or proteoglycan producing feeder cells).

BRIEF DRAWING DESCRIPTIONS

FIGS. 3A-3D illustrates new stem cell lines derived in absence of feeder cells, using the indicated media.

FIGS. 6A-6F illustrate morphology of stem cell colonies after multiple passages in the exemplary invention media formulation: A) stem cell colony grown in conditioned media 4×(control); B) two days after $4^{th}$ passage in exemplary invention media, with no addition of hyaluronidase 4×; C) two days after $2^{nd}$ passage in exemplary invention media 4×; D) Two days after the $3^{rd}$ passage in exemplary invention media 4×; E) Two days after the $5^{th}$ passage in exemplary invention media 4×; and F) stem cells inside of a colony after $5^{th}$ passages in exemplary invention media appear very healthy with minimal floating debris, large nucleus with prominent nucleolus (20×).

FIGS. 7A-7C illustrate that "sternness" was preserved after 5 passages: A) Oct4 labeling of a stem cell colony; B) nuclear counterstain (bisbenzimide); and C) Imposed: pink Oct4 labeled stem cells, blue differentiated cells.

FIGS. 8A-8C illustrate in vitro differentiation of cultures grown in exemplary invention media supplemented with hyaluronidase: A) Nestin positive cells specific for ectoderm; B) alpha feto-protein positive cells for endodermal lineages; and C) smooth muscle actin positive cells for mesodermal lineages.

Figure 9:
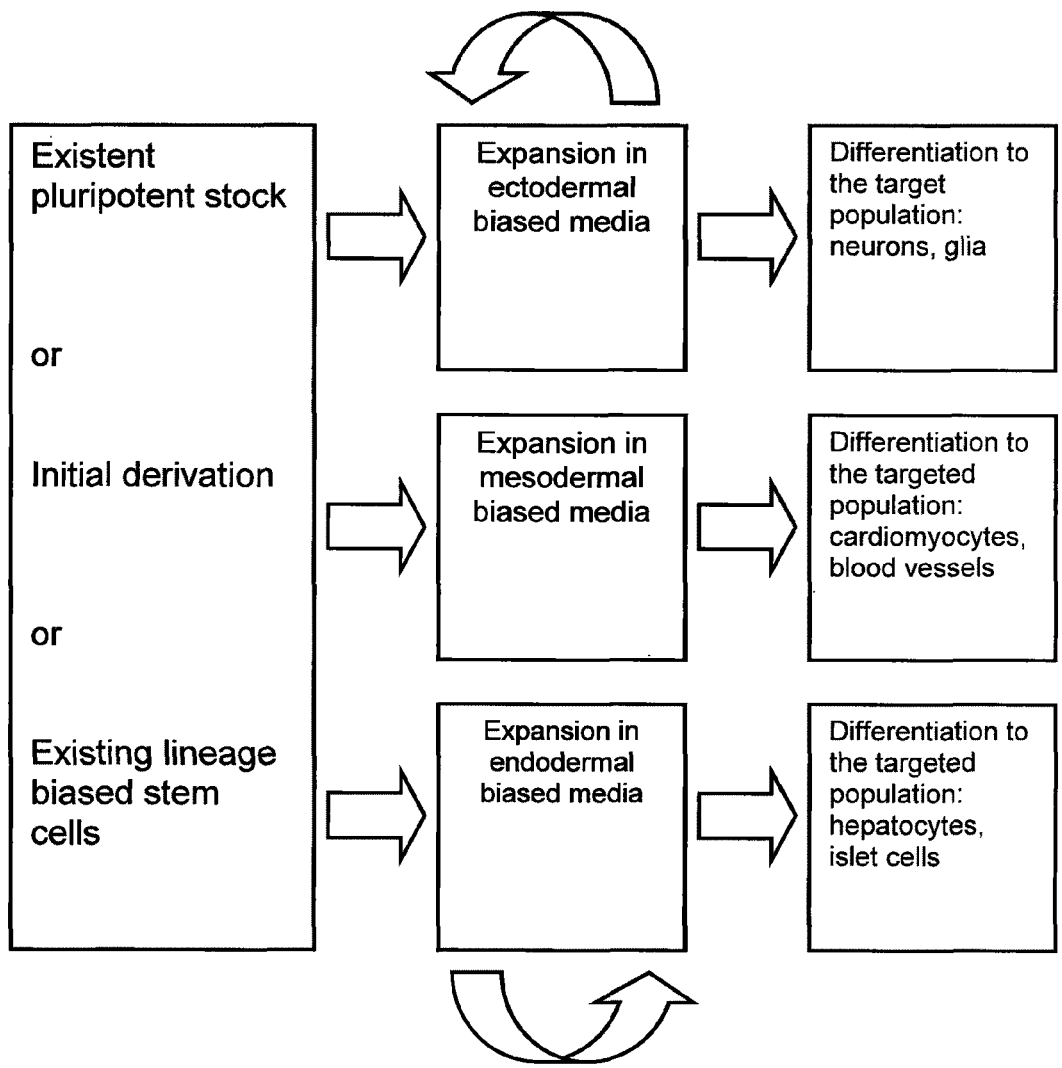

FIG. 9 illustrates that instead of expanding the stem cells in a fully balanced and pluripotent media, the use of a "biased" media is possible when certain embryonic germ layer lineages are targeted.

Figure 10A:
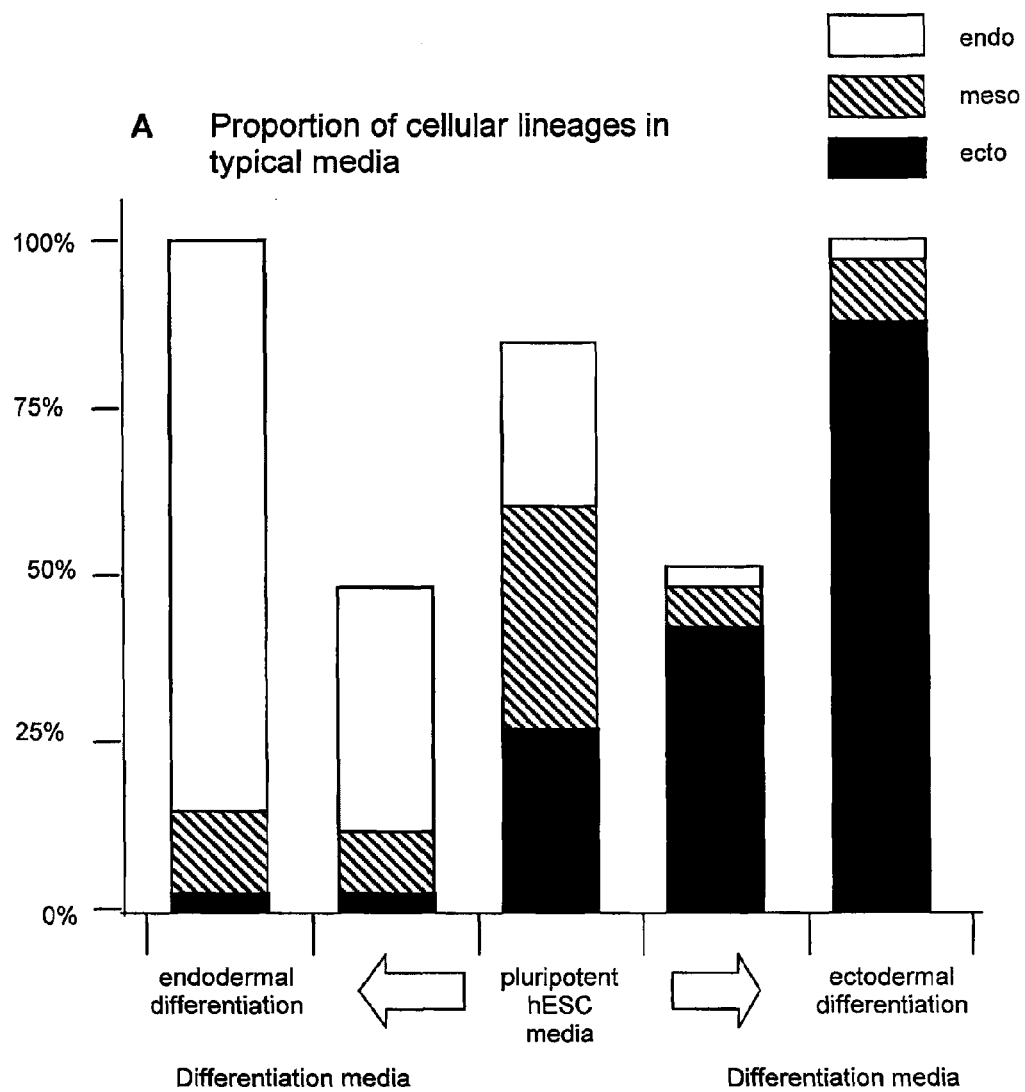
Figure 10B:
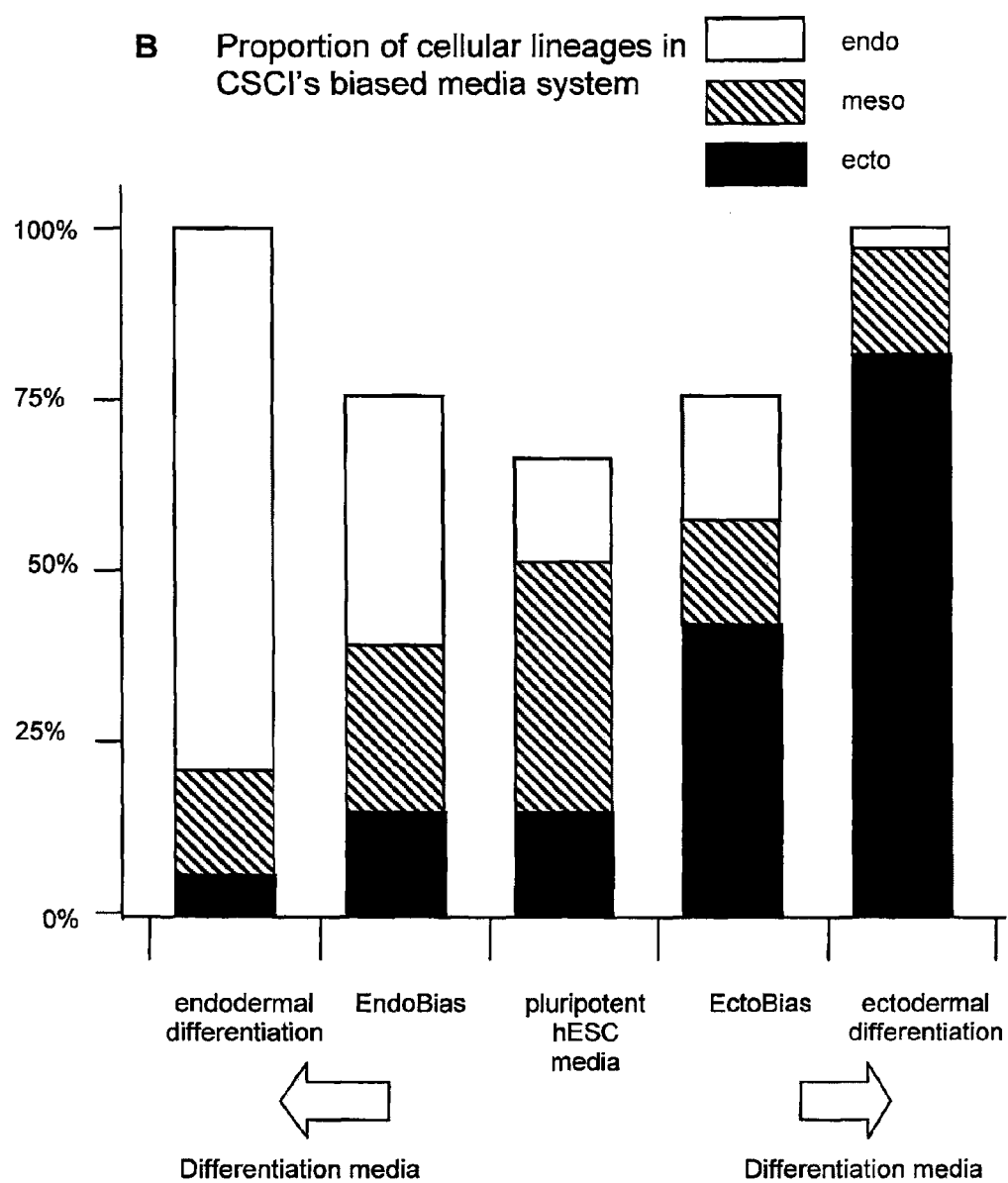

FIGS. 10A-10B show that A) when differentiation is initiated in a typical differentiation media, there is an initial drop in the number of cells which reduces the efficiency of the differentiation; and B) when exemplary invention media is used to expand the stem cells for multiple passages, the initial drop in the cell population is avoided significantly increasing yield and efficiency of differentiation.

DETAILED DESCRIPTION

The invention provides media formulations. In one embodiment, a complete media formulation includes the following components: albumin, an iron carrier, glutamine, a glycosidase or hydrolase, fibroblast growth factor (FGF), a salt or mineral, and essential amino acids, at an osmolarity of about 220-330 mOsm/Liter. In another embodiment, a complete media formulation of the invention includes the following components: albumin, an iron carrier, glutamine, a glycosaminoglycan degradation product, fibroblast growth factor (FGF), a salt or mineral, and essential amino acids, at an osmolarity of about 220-330 mOsm/Liter. Media formulations include formulations compatible with survival or proliferation of cells.

A complete media formulation is a mixture of components which, when used under appropriate conditions (e.g., at appropriate concentrations or dilutions, pH, temperature, % $CO_2$ or % $O_2$) are compatible with survival or proliferation of cells. Such media formulations are sufficient to maintain or sustain cell viability for at least a period of time, whether the cells proliferate or not, or whether the cells differentiate or not. The terms "media composition or media preparation" can be used interchangeably with "media formulation." The term "culture media" can also be used to refer to a media formulation that is able to maintain or sustain viability of one or a plurality of cells for at least a period of time. A "cell culture" as used herein refers to one or a plurality of cells whose cell viability is maintained or sustained for at least a period of time. Not all cells are required to survive or proliferate in a complete media formulation of the invention and, in fact a small or even a large number of cells may die or senesce. Likewise, not all cells of a given cell culture are required to survive or proliferate in a complete media formulation of the invention.

"Components" refer to particular compounds or ingredients that are present or make up a media formulation. Such components can be used in the media to sustain or maintain cell survival, viability or proliferation. Such components can be unrelated to cell survival, viability or proliferation, but may serve another purpose, such as a preservative, dye or coloring agent (e.g., to indicate pH of the media).

A media formulation can be complete or incomplete. A "complete" media formulation includes appropriate types and amounts of components adequate to be compatible with survival or proliferation of cells. An "incomplete" media formulation typically lacks one or more components as compared to a complete media formulation, although lack of a particular component does not necessarily make an incomplete media formulation inadequate or insufficient to be compatible with survival or proliferation of cells.

Media formulations of the invention include components in amounts compatible with survival of cells such as stem cells, tissue specific, germinal or adult, whether totipotent, multipotent or pluripotent. Media formulations of the invention also include components in amounts compatible with survival of stem cells without substantial differentiation of the stem cells. The term "without substantial differentiation," when used in reference to stem cells, means that no more than about 20%, +/−5%, of the total number of stem cells in a given stem cell population have begun to differentiate or have differentiated. This term can be used to refer to one or a plurality of passages, e.g., 2, 3, 4, 5 or more passages, of a cell culture that includes stem cells.

Stem cells are characterized typically by morphology as well as the presence of characteristic markers. For example, morphology of a stem cell is typically dense, well delimited small cells with a large nucleus representing about 80 to 95% of the total cellular volume. Stem cell differentiation can result in a phenotypic change—the most commonly observed change is in cell morphology. For example, the proportion of nucleus to cytoplasm is reduced, cells acquire migratory capability, and the colony edges become less defined. Stem cell differentiation can also result in a loss of stem cell markers (e.g., OCT4, SSEA4, TRA1-81) or telomerase activity. Stem cell differentiation can further result in acquiring markers or morphologies characteristic of one or more of the three embryonic germ layers—ectoderm, mesoderm or endoderm. Under certain conditions, stem cells can grow outside of stem cell colonies and their number and the growth can be determined by immunolabeling with markers characteristic of stem cells.

Spontaneous differentiation of stem cells is normal and reflects normal functioning stem cells. Spontaneous differentiation results in a cellular mass-stroma—which fills the space between the colonies. The proportion between the stroma representing differentiated cells and colonies representing non-differentiated cells can vary, as long as the stem cell colonies are properly defined (delimitation, dense, typical cellular content). Stem cells can be a single colony in a culture dish (which can be 0.1% of the total cell number) to virtually 100% with a complete absence of stromal cells. The proportion between stroma (differentiated cells) and colonies (stem cells) in media can be regulated by other factors unrelated to the media composition, for example the ratio that cells are split when passaged.

Media formulations of the invention can include, for example, albumin. Albumins play a role in various functions, such as transporting fatty acids, thyroid and steroid hormones and other substances. Albumins also contribute to maintaining osmotic pressure of extracellular fluid. Non-limiting examples of albumins include mammalian albumins, such as primate (e.g., human) and bovine serum albumin (BSA), goat serum albumin (GSA), rabbit serum albumin (RSA). Additional specific examples of albumins include probumin (Chemicon) and ICPBio albumin, highly purified forms of BSA that are virus/endotoxin free.

Amounts or concentrations of albumin appropriate in media formulations of the invention are from about 1 to about 100 g/L. Additional non-limiting examples of amounts or concentrations of albumin appropriate in media formulations of the invention are from about 1 to about 50 g/L, 1 to about 25 g/L, or 1 to about 5 g/L. Albumins are susceptible to pH below 6, exposure to light and temperatures that cause protein denaturation. Albumin stock solutions can be frozen at −20° C. A concentrated solution of 10-40% can be frozen for long periods of time.

Media formulations of the invention can include, for example, an iron carrier. Iron is an essential trace element for cells but can be toxic in the free form. An iron carrier is typically a ligand for transferrin receptor. A non-limiting example of an iron carrier is therefore transferrin. Iron carriers can be mammalian, such as primate (e.g., human) or ungulate (e.g., bovine, goat, equine or porcine).

Amounts or concentrations of iron carrier appropriate in media formulations of the invention are from about 5 to about 100 ug/mL. Additional non-limiting examples of amounts or concentrations of iron carrier appropriate in media formulations of the invention are from about 10 to about 50 ug/mL, 15 to about 25 ug/mL, or about 20 ug/mL. Transferrin stock solutions can be frozen long term or refrigerated for shorter time periods. Transferrin can withstand repeated freezing and thawing. Transferrin is sensitive to pH changes and temperatures greater than 60° C.

Media formulations of the invention can include, for example, glutamine, which can also be referred to as glutamate. Glutamine is involved in a variety of cell metabolic processes. Glutamine can be converted to glucose, which can be used as a carbon energy source. Glutamine in combination with N-acetyl cysteine promotes the synthesis of glutathione, an antioxidant. Glutamine can be provided as a monomer, or as a di-, tri-, tetra-, penta-hexa-, hepta-, or larger peptide. One non-limiting example of a glutamine di-peptide is glutamine-alanine.

Amounts or concentrations of glutamine appropriate in media formulations of the invention are from about 10 to about 50 mg/mL. Additional non-limiting examples of amounts or concentrations of glutamine appropriate in media formulations of the invention are from about 10 to about 40 mg/mL, 15 to about 30 mg/mL, or about 25 mg/mL. Glutamine stock solution is typically stored frozen, but can be stored for short periods of time at refrigeration temperatures.

Media formulations of the invention can include, for example, a glycosidase or hydrolase. As used herein, the terms glycosidase or hydrolase refer to an enzyme that is capable of cleaving a GAG glycosidic linkage (O- or S-glycosyl) thereby hydrolyzing GAGs. Glycosidases and hydrolases vary with respect to origin, substrate specificity, and mechanism of action. Glycosidases and hydrolases include soluble forms and membrane bound forms. A soluble glycosidase or hydrolase means that the enzyme is at least partially soluble in the media formulation, and membrane bound glycosidase or hydrolase means that the enzyme is tethered or anchored to a lipid, such as a lipid bilayer of a cell membrane.

Non-limiting examples of glycosidases or hydrolases include hyaluronidases, which can cleave hyaluronic acids or chondroitin sulfates. Mammalian-type hyaluronidases (e.g., Hyal1, Hyal2, Hyal3, Hya4 and PH204) are endo-beta-N-acetylhexosaminidases with produce tetrasaccharides and hexasaccharides as end products. Mammalian-type hyaluronidases typically have hydrolytic and transglycosidase activities, and can degrade hyaluronan, chondroitin and chondroitin sulfates. Mammalian hyaluronidases include enzymes active at neutral pH and enzymes active at acid pH. Mammalian hyaluronidases Hyal1, Hyal2 and Hyal3 cleave the glycosidic linkage between the glucuronic acid component and the N-acetyl galactosamine component of the HA to produce tetra and hexasaccharides. Hyal1 is the prototypical acid-active enzyme and PH204 is the prototypical neutral-active enzyme. Hyal1 has been reported to lack detectable activity in vitro above pH 4.5. Hyal4 is a chondroitinase and lacks activity towards hyaluronan. Hyal2 is an acid active enzyme.

Bacterial hyaluronidases degrade hyaluronan and, and to various extents, CS and DS. They are endo-beta-N-acetylhexosaminidases that operate by a beta elimination reaction that yields primarily disaccharide end products. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Non-limiting examples of glycosidases or hydrolases also include N-glycosidase F, which can cleave dermatan sulfate.

Non-limiting examples of glycosidases or hydrolases also include chondroitinases, which can cleave chondroitin sulfate through an endoglycosidase reaction. Specific examples of chondroitinases include chondroitinase ABC (Suzuki, et al., *J. Biol. Chem.*, 243:1543 (1968)), chondroitinase AC (Yamagata et al., *J. Biol. Chem.* 243:1523 (1968)), chondroitinase AC II (Hiyama and Okada, *J. Biol. Chem.*, 250:1824 (1975), hyaluronidase ACIII (Miyazono et al., *Seikagaku*, 61:1023 (1989)), chondroitinase B (Michelacci and Dietrich, *Biochem. Biophys. Res. Commun.*, 56:973 (1974), and chondroitinase C (Miyazono, et al., *Seikagaku*, 61:1023 (1939)).

Non-limiting examples of glycosidases or hydrolases further include heparanase or glycosidase, which can cleave heparin or heparan sulfate. Heparanase is an endo-β-D-glucuronidase that cleaves the β-1,4-glycosidic bond between a D-glucuronate and a D-glucosamine in heparan sulfate.

Non-limiting examples of glycosidases or hydrolases additionally include keratan sulfate hydrolases, which can cleave keratan sulfate. Specific examples of keratan sulfate hydrolases include endo-β-N-acetylglucosaminidase.

Further specific non-limiting examples of glycosidases or hydrolases are as set forth in Table 1:
Table 1
EC 3.2.1 class Glycosidases/Hydrolases that hydrolyze O- and S-glycosyl GAGs
EC 3.2.1.1 α-amylase
EC 3.2.1.2 β-amylase
EC 3.2.1.3 glucan 1,4-α-glucosidase
EC 3.2.1.4 cellulase
EC 3.2.1.6 endo-1,3(4)-β-glucanase
EC 3.2.1.7 inulinase
EC 3.2.1.8 endo-1,4-β-xylanase
EC 3.2.1.10 oligo-1,6-glucosidase
EC 3.2.1.11 dextranase
EC 3.2.1.14 chitinase
EC 3.2.1.15 polygalacturonase
EC 3.2.1.17 lysozyme EC 3.2.1.18 exo-α-sialidase
EC 3.2.1.20 α-glucosidase
EC 3.2.1.21 β-glucosidase
EC 3.2.1.22 α-galactosidase
EC 3.2.1.23 β-galactosidase
EC 3.2.1.24 α-mannosidase
EC 3.2.1.25 β-mannosidase
EC 3.2.1.26 β-fructofuranosidase
EC 3.2.1.28 α,α-trehalase
EC 3.2.1.31 β-glucuronidase
EC 3.2.1.32 xylan endo-1,3-β-xylosidase
EC 3.2.1.33 amylo-1,6-glucosidase
EC 3.2.1.35 hyaluronoglucosaminidase
EC 3.2.1.36 hyaluronoglucuronidase
EC 3.2.1.37 xylan 1,4-β-xylosidase
EC 3.2.1.38 β-D-fucosidase
EC 3.2.1.39 glucan endo-1,3-β-D-glucosidase
EC 3.2.1.40 α-L-rhamnosidase
EC 3.2.1.41 pullulanase
EC 3.2.1.42 GDP-glucosidase
EC 3.2.1.43 β-L-rhamnosidase
EC 3.2.1.44 fucoidanase
EC 3.2.1.45 glucosylceramidase
EC 3.2.1.46 galactosylceramidase
EC 3.2.1.47 galactosylgalactosylglucosylceramidase
EC 3.2.1.48 sucrose α-glucosidase
EC 3.2.1.49 α-N-acetylgalactosaminidase
EC 3.2.1.50 α-N-acetylglucosaminidase
EC 3.2.1.51 α-L-fucosidase
EC 3.2.1.52 β-L-N-acetylhexosaminidase
EC 3.2.1.53 β-N-acetylgalactosaminidase
EC 3.2.1.54 cyclomaltodextrinase
EC 3.2.1.55 α-N-arabinofuranosidase
EC 3.2.1.56 glucuronosyl-disulfoglucosamine glucuronidase
EC 3.2.1.57 isopullulanase
EC 3.2.1.58 glucan 1,3-β-glucosidase
EC 3.2.1.59 glucan endo-1,3-α-glucosidase
EC 3.2.1.60 glucan 1,4-α-maltotetraohydrolase
EC 3.2.1.61 mycodextranase
EC 3.2.1.62 glycosylceramidase
EC 3.2.1.63 1,2-α-L-fucosidase
EC 3.2.1.64 2,6-β-fructan 6-levanbiohydrolase
EC 3.2.1.65 levanase
EC 3.2.1.66 quercitrinase
EC 3.2.1.67 galacturan 1,4-α-galacturonidase
EC 3.2.1.68 isoamylase
EC 3.2.1.70 glucan 1,6-α-glucosidase
EC 3.2.1.71 glucan endo-1,2-β-glucosidase
EC 3.2.1.72 xylan 1,3-β-xylosidase
EC 3.2.1.73 licheninase
EC 3.2.1.74 glucan 1,4-β-glucosidase
EC 3.2.1.75 glucan endo-1,6-β-glucosidase
EC 3.2.1.76 L-iduronidase
EC 3.2.1.77 mannan 1,2-(1,3)-α-mannosidase
EC 3.2.1.78 mannan endo-1,4-β-mannosidase
EC 3.2.1.80 fructan β-fructosidase
EC 3.2.1.81 β-agarase
EC 3.2.1.82 exo-poly-α-galacturonosidase
EC 3.2.1.83 κ-carrageenase
EC 3.2.1.84 glucan 1,3-α-glucosidase
EC 3.2.1.85 6-phospho-β-galactosidase
EC 3.2.1.86 6-phospho-β-glucosidase
EC 3.2.1.87 capsular-polysaccharide endo-1,3-α-galactosidase
EC 3.2.1.88 β-L-arabinosidase
EC 3.2.1.89 arabinogalactan endo-1,4-β-galactosidase
EC 3.2.1.91 cellulose 1,4-β-cellobiosidase
EC 3.2.1.92 peptidoglycan β-N-acetylmuramidase
EC 3.2.1.93 α,α-phosphotrehalase
EC 3.2.1.94 glucan 1,6-α-isomaltosidase
EC 3.2.1.95 dextran 1,6-α-isomaltotriosidase
EC 3.2.1.96 mannosyl-glycoprotein endo-β-N-acetylglucosaminidase
EC 3.2.1.97 glycopeptide α-N-acetylgalactosaminidase
EC 3.2.1.98 glucan 1,4-α-maltohexaosidase
EC 3.2.1.99 arabinan endo-1,5-α-L-arabinosidase
EC 3.2.1.100 mannan 1,4-mannobiosidase
EC 3.2.1.101 mannan endo-1,6-α-mannosidase
EC 3.2.1.102 blood-group-substance endo-1,4-β-galactosidase
EC 3.2.1.103 keratan-sulfate endo-1,4-β-galactosidase
EC 3.2.1.104 steryl-β-glucosidase
EC 3.2.1.105 strictosidine β-glucosidase
EC 3.2.1.106 mannosyl-oligosaccharide glucosidase
EC 3.2.1.107 protein-glucosylgalactosylhydroxylysine glucosidase
EC 3.2.1.108 lactase
EC 3.2.1.109 endogalactosaminidase
EC 3.2.1.110 mucinaminylserine mucinaminidase
EC 3.2.1.111 1,3-α-L-fucosidase
EC 3.2.1.112 2-deoxyglucosidase
EC 3.2.1.113 mannosyl-oligosaccharide 1,2-α-mannosidase
EC 3.2.1.114 mannosyl-oligosaccharide 1,3-1,6-α-mannosidase
EC 3.2.1.115 branched-dextran exo-1,2-α-glucosidase
EC 3.2.1.116 glucan 1,4-α-maltotriohydrolase
EC 3.2.1.117 amygdalin β-glucosidase
EC 3.2.1.118 prunasin β-glucosidase
EC 3.2.1.119 vicianin β-glucosidase
EC 3.2.1.120 oligoxyloglucan β-glycosidase
EC 3.2.1.121 polymannuronate hydrolase
EC 3.2.1.122 maltose-6'-phosphate glucosidase
EC 3.2.1.123 endoglycosylceramidase
EC 3.2.1.124 3-deoxy-2-octulosonidase
EC 3.2.1.125 raucaffricine β-glucosidase
EC 3.2.1.126 coniferin β-glucosidase
EC 3.2.1.127 1,6-α-L-fucosidase
EC 3.2.1.128 glycyrrhizinate β-glucuronidase
EC 3.2.1.129 endo-α-sialidase
EC 3.2.1.130 glycoprotein endo-α-1,2-mannosidase
EC 3.2.1.131 xylan α-1,2-glucuronosidase
EC 3.2.1.132 chitosanase
EC 3.2.1.133 glucan 1,4-α-maltohydrolase
EC 3.2.1.134 difructose-anhydride synthase
EC 3.2.1.135 neopullulanase
EC 3.2.1.136 glucuronoarabinoxylan endo-1,4-β-xylanase
EC 3.2.1.137 mannan exo-1,2-1,6-α-mannosidase
EC 3.2.1.138 now EC 4.2.2.15
EC 3.2.1.139 α-glucuronidase
EC 3.2.1.140 lacto-N-biosidase
EC 3.2.1.141 4-α-D-{(14)-α-D-glucano}trehalose trehalohydrolase
EC 3.2.1.142 limit dextrinase
EC 3.2.1.143 poly(ADP-ribose) glycohydrolase
EC 3.2.1.144 3-deoxyoctulosonase
EC 3.2.1.145 galactan 1,3-β-galactosidase
EC 3.2.1.146 β-galactofuranosidase
EC 3.2.1.147 thioglucosidase
EC 3.2.1.148 now EC 4.4.1.21
EC 3.2.1.149 β-primeverosidase
EC 3.2.1.150 oligoxyloglucan reducing-end-specific cellobiohydrolase
EC 3.2.1.151 xyloglucan-specific endo-β-1,4-glucanase
EC 3.2.1.152 mannosylglycoprotein endo-β-mannosidase EC 3.2.1.153 fructan β-(2,1)-fructosidase
EC 3.2.1.154 fructan β-(2,6)-fructosidase
EC 3.2.1.155 xyloglucan-specific exo-β-1,4-glucanase
EC 3.2.1.156 oligosaccharide reducing-end xylanase
EC 3.2.1.157 ι-carrageenase
EC 3.2.1.158 α-agarase
EC 3.2.1.159 α-neoagaro-oligosaccharide hydrolase
EC 3.2.1.160 deleted, identical to EC 3.2.1.155
EC 3.2.1.161 β-apiosyl-β-glucosidase Sequences of particular glycosidases or hydrolases are as follows:

```
HYAL1_HUMAN Hyaluronidase-1 - Homo sapiens (Human).
MAAHLLPICALFLTLLDMAQGFRGPLLPNRPFTTVWNANTQWCLERHGVDVDVSVFDV

VANPGQTFRGPDMTIFYSSQLGTYPYYTPTGEPVFGGLPQNASLIAHLARTFQDILAAIPA

PDFSGLAVIDWEAWRPRWAFNWDTKDIYRQRSRALVQAQHPDWPAPQVEAVAQDQF

QGAARAWMAGTLQLGRALRPRGLWGFYGFPDCYNYDFLSPNYTGQCPSGIRAQNDQL

GWLWGQSRALYPSIYMPAVLEGTGKSQMYVQHRVAEAFRVAVAAGDPNLPVLPYVQI

FYDTTNHFLPLDELEHSLGESAAQGAAGVVLWVSWENTRTKESCQAIKEYMDTTLGPFI

LNVTSGALLCSQALCSGHGRCVRRTSHPKALLLLNPASFSIQLTPGGGPLSLRGALSLED

QAQMAVEFKCRCYPGWQAPWCERKSMW;

HYAL1_BOVIN Hyaluronidase-1 - Bos taurus (Bovine).
MRPFSLEVSLHLPWAMAAHLLPVCTLFLNLLSMTQGSRDPVVPNQPFTTIWNANTEWC

MKKHGVDVDISIFDVVTNPGQTFRGPNMTIFYSSQLGTYPYYTSAGEPVFGGLPQNASL

NAHLARTFQDILAAMPEPRFSGLAVIDWEAWRPRWAFNWDTKDIYRQRSRALVQKQH

PDWLAPRVEAAAQDQFEGAAEEWMAGTLKLGQALRPQGLWGFYNFPECYNYDFKSPN

YTGRCPLNICAQNDQLGWLWGQSRALYPSIYLPAALEGTKKTQMFVQHRVAEAFRVAA

GAGDPKLPVLPYMQLFYDMTNHFLPAEELEHSLGESAAQGAAGVVLWVSWLSTSTKES

CQAIKEYVDTTLGPSILNVTSGARLCSQVLCSGHGRCARRPSYPKARLILNSTSFSIKPTP

GGGPLTLQGALSLEDRLRMAVEFECRCYRGWRGTRCEQWGMW;

HYAL1_MOUSE Hyaluronidase-1 - Mus musculus (Mouse).
MLGLTQHAQKVWRMKPFSPEVSPGSSPATAGHLLRISTLFLTLLELAQVCRGSVVSNRP

FITVWNGDTHWCLTEYGVDVDVSVFDVVANKEQSFQGSNMTIFYREELGTYPYYTPTG

EPVFGGLPQNASLVTHLAHTFQDIKAAMPEPDFSGLAVIDWEAWRPRWAFNWDSKDIY

RQRSMELVQAEHPDWPETLVEAAAKNQFQEAAEAWMAGTLQLGQVLRPRGLWGYYG

FPDCYNNDFLSLNYTGQCPVFVRDQNDQLGWLWNQSYALYPSIYLPAALMGTGKSQM

YVRHRVQEALRVAIVSRDPHVPVMPYVQIFYEMTDYLLPLEELEHSLGESAAQGVAGA

VLWLSSDKTSTKESCQAIKAYMDSTLGPFIVNVTSAALLCSEALCSGHGRCVRHPSYPE

ALLTLNPASFSIELTHDGRPPSLKGTLSLKDRAQMAMKFRCRCYRGWRGKWCDKRGM;

HYAL2_HUMAN Hyaluronidase-2 - Homo sapiens (Human).
MRAGPGPTVTLALVLAVAWAMELKPTAPPIFTGRPFVVAWDVPTQDCGPRLKVPLDLN

AFDVQASPNEGFVNQNITIFYRDRLGLYPRFDSAGRSVHGGVPQNVSLWAHRKMLQKR

VEHYIRTQESAGLAVIDWEDWRPVWVRNWQDKDVYRRLSRQLVASRHPDWPPDRIVK

QAQYEFEFAAQQFMLETLRYVKAVRPRHLWGFYLFPDCYNHDYVQNWESYTGRCPDV

EVARNDQLAWLWAESTALFPSVYLDETLASSRHGRNFVSFRVQEALRVARTHHANHAL

PVYVFTRPTYSRRLTGLSEMDLISTIGESAALGAAGVILWGDAGYTTSTETCQYLKDYLT

RLLVPYVVNVSWATQYCSRAQCHGHGRCVRRNPSASTFLHLSTNSFRLVPGHAPGEPQ

LRPVGELSWADIDHLQTHFRCQCYLGWSGEQCQWDHRQAAGGASEAWAGSHLTSLLA

LAALAFTWTL;
```

```
-continued
HYAL2_MOUSE Hyaluronidase-2 - Mus musculus (Mouse).
MRAGLGPIITLALVLEVAWAGELKPTAPPIFTGRPFVVAWNVPTQECAPRHKVPLDLRA

FDVKATPNEGFFNQNITTFYYDRLGLYPRFDAAGTSVHGGVPQNGSLCAHLPMLKESVE

RYIQTQEPGGLAVIDWEEWRPVWVRNWQEKDVYRQSSRQLVASRHPDWPSDRVMKQ

AQYEFEFAARQFMLNTLRYVKAVRPQHLWGFYLFPDCYNHDYVQNWESYTGRCPDVE

VARNDQLAWLWAESTALFPSVYLDETLASSVHSRNFVSFRVREALRVAHTHHANHALP

VYVFTRPTYTRGLTGLSQVDLISTIGESAALGSAGVIFWGDSEDASSMETCQYLKNYLTQ

LLVPYIVNVSWATQYCSWTQCHGHGRCVRRNPSANTFLHLNASSFRLVPGHTPSEPQLR

PEGQLSEADLNYLQKHFRCQCYLGWGGEQCQRNYKGAAGNASRAWAGSHLTSLLGLV

AVALTWTL;

HYAL3_HUMAN Hyaluronidase-3 - Homo sapiens (Human).
MTTQLGPALVLGVALCLGCGQPLPQVPERPFSVLWNVPSAHCEARFGVHLPLNALGIIA

NRGQHFHGQNMTIFYKNQLGLYPYFGPRGTAHNGGIPQALPLDRHLALAAYQIHHSLRP

GFAGPAVLDWEEWCPLWAGNWGRRRAYQAASWAWAQQVFPDLDPQEQLYKAYTGF

EQAARALMEDTLRVAQALRPHGLWGFYHYPACGNGWHSMASNYTGRCHAATLARNT

QLHWLWAASSALFPSIYLPPRLPPAHHQAFVRHRLEEAFRVALVGHRHPLPVLAYVRLT

HRRSGRFLSQDDLVQSIGVSAALGAAGVVLWGDLSLSSSEEECWHLHDYLVDTLGPYVI

NVTRAAMACSHQRCHGHGRCARRDPGQMEAFLHLWPDGSLGDWKSFSCHCYWGWA

GPTCQEPRPGPKEAV;
and

HYAL4_HUMAN Hyaluronidase 4 - Homo sapiens (Human).
MKVLSEGQLKLCVVQPVHLTSWLLIFFILKSISCLKPARLPIYQRKPFIAAWNAPTDQCLI

KYNLRLNLKMFPVIGSPLAKARGQNVTIFYVNRLGYYPWYTSQGVPINGGLPQNISLQV

HLEKADQDINYYIPAEDFSGLAVIDWEYWRPQWARNWNSKDVYRQKSRKLISDMGKN

VSATDIEYLAKVTFEESAKAFMKETIKLGIKSRPKGLWGYYLYPDCHNYNVYAPNYSGS

CPEDEVLRNNELSWLWNSSAALYPSICVWKSLGDSENILRFSKFRVHESMRISTMTSHD

YALPVFVYTRLGYRDEPLFFLSKQDLVSTIGESAALGAAGIVIWGDMNLTASKANCTKV

KQFVSSDLGSYIANVTRAAEVCSLHLCRNNGRCIRKMWNAPSYLHLNPASYHIEASEDG

EFTVKGKASDTDLAVMADTFSCHCYQGYEGADCREIKTADGCSGVSPSPGSLMTLCLL

LLASYRSIQL.
```

For cells such as stem cells, a glycosidase or hydrolase can be added periodically to media or to cells in a culture media. A glycosidase or hydrolase can be added to media or to cell cultures, for example, hourly, daily, or when adding fresh media or a media supplement to a cell culture, such as a stem cell culture.

Glycosidase or hydrolase amounts or concentrations appropriate in media formulations of the invention are from about 1 to about 100 ug/ml. Additional non-limiting examples of amounts or concentrations of glycosidase or hydrolase appropriate in media formulations of the invention are from about 1 to about 50 ug/ml, 1 to about 25 ug/ml, 1 to about 10 ug/ml. Glycosidases and hydrolases (e.g., hyaluronidases) typically become slowly inactivated in solution. Glycosidase and hydrolase powder and stock solutions are typically frozen at about −20° C. for long term storage. Repeated freeze/thaw cycles typically result in loss of activity. After reconstitution, glycosidases and hydrolases are stable in solution at 4° C. for about 7-30 days, and may be used for up to one week.

Media formulations of the invention can include, for example, a fibroblast growth factor (FGF). FGF promotes or sustains fibroblast cell viability, survival, growth or proliferation. FGFs are associated with many developmental processes including mesoderm induction, antero-posterior patterning, neural induction, angiogenesis, axon extension and limb formation.

Non-limiting examples of a fibroblast growth factor acidic FGF (aFGF, also referred to as FGF-1) and basic FGF (bFGF, also referred to as FGF-2). FGF1 is a heparin-binding growth factors, which has angiogenic activity in vivo and is a potent mitogen for a variety of cell types in vitro. FGF1 binds FGFR2 and forms a ternary complex containing 2 molecules each of FGFR2 and FGF1 for 1 heparin molecule. FGF2 promotes the endothelial cell proliferation and the physical organization of endothelial cells into tube-like structures. It thus promotes angiogenesis, the growth of new blood vessels from the pre-existing vasculature. As well as stimulating blood vessel growth, FGF2 participates in wound healing, for example, it stimulates proliferation of fibroblasts that give rise to granulation tissue, which fills up a wound space/cavity early in the wound healing process. FGF2 in vitro has mitogenic activity, stimulating proliferation of various cell types.

Additional specific examples of FGF include FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. Sequences of these and other FGFs are as follows:

```
FGF1_HUMAN Heparin-binding growth factor 1 - Homo sapiens (Human).
MAEGEITTFTALTEKFNLPPGNYKKPKLLYCSNGGHFLRILPDGTVDGTRDRSDQHIQLQ

LSAESVGEVYIKSTETGQYLAMDTDGLLYGSQTPNEECLFLERLEENHYNTYISKKHAE

KNWFVGLKKNGSCKRGPRTHYGQKAILFLPLPVSSD;

FGF1_MOUSE Heparin-binding growth factor 1 - Mus musculus (Mouse).
MAEGEITTFAALTERFNLPLGNYKKPKLLYCSNGGHFLRILPDGTVDGTRDRSDQHIQLQ

LSAESAGEVYIKGTETGQYLAMDTEGLLYGSQTPNEECLFLERLEENHYNTYTSKKHAE

KNWFVGLKKNGSCKRGPRTHYGQKAILFLPLPVSSD;

FGF2_HUMAN Heparin-binding growth factor 2 - Homo sapiens (Human).
MAAGSITTLPALPEDGGSGAFPPGHFKDPKRLYCKNGGFFLRIHPDGRVDGVREKSDPHI

KLQLQAEERGVVSIKGVCANRYLAMKEDGRLLASKCVTDECFFFERLESNNYNTYRSR

KYTSWYVALKRTGQYKLGSKTGPGQKAILFLPMSAKS;

FGF2_MOUSE Heparin-binding growth factor 2 - Mus musculus (Mouse).
MAASGITSLPALPEDGGAAFPPGHFKDPKRLYCKNGGFFLRIHPDGRVDGVREKSDPHV

KLQLQAEERGVVSIKGVCANRYLAMKEDGRLLASKCVTEECFFFERLESNNYNTYRSR

KYSSWYVALKRTGQYKLGSKTGPGQKAILFLPMSAKS;

FGF3_HUMAN INT-2 proto-oncogene protein - Homo sapiens (Human).
MGLIWLLLLSLLEPGWPAAGPGARLRRDAGGRGGVYEHLGGAPRRRKLYCATKYHLQ

LHPSGRVNGSLENSAYSILEITAVEVGIVAIRGLFSGRYLAMNKRGRLYASEHYSAECEF

VERIHELGYNTYASRLYRTVSSTPGARRQPSAERLWYVSVNGKGRPRRGFKTRRTQKSS

LFLPRVLDHRDHEMVRQLQSGLPRPPGKGVQPRRRRQKQSPDNLEPSHVASRLGSQLEA

SAH;

FGF4_HUMAN Fibroblast growth factor 4 - Homo sapiens (Human).
MSGPGTAAVALLPAVLLALLAPWAGRGGAAAPTAPNGTLEAELERRWESLVALSLARL

PVAAQPKEAAVQSGAGDYLLGIKRLRRLYCNVGIGFHLQALPDGRIGGAHADTSLLELS

PVERGVVSIFGVASRFFVAMSSKGKLYGSPFFTDECTFKEILLPNNYNAYESYKYPGMFI

ALSKNGKTKKGNRVSPTMKVTHFLPRL;

FGF5_HUMAN Fibroblast growth factor 5 - Homo sapiens (Human).
MSLSFLLLLFFSHLILSAWAHGEKRLAPKGQPGPAATDRNPRGSSSRQSSSSAMSSSSASS

SPAASLGSQGSGLEQSSFQWSPSGRRTGSLYCRVGIGFHLQIYPDGKVNGSHEANMLSV

LEIFAVSQGIVGIRGVFSNKFLAMSKKGKLHASAKFTDDCKFRERFQENSYNTYASAIHR

TEKTGREWYVALNKRGKAKRGCSPRVKPQHISTHFLPRFKQSEQPELSFTVTVPEKKKP

PSPIKPKIPLSAPRKNTNSVKYRLKFRFG;

FGF6_HUMAN Fibroblast growth factor 6 - Homo sapiens (Human).
MALGQKLFITMSRGAGRLQGTLWALVFLGILVGMVVPSPAGTRANNTLLDSRGWGTLL

SRSRAGLAGEIAGVNWESGYLVGIKRQRRLYCNVGIGFHLQVLPDGRISGTHEENPYSLL

EISTVERGVVSLFGVRSALFVAMNSKGRLYATPSFQEECKFRETLLPNNYNAYESDLYQ

GTYIALSKYGRVKRGSKVSPIMTVTHFLPRI;
```

-continued

FGF7_HUMAN Keratinocyte growth factor - Homo sapiens (Human).
MHKWILTWILPTLLYRSCFHIICLVGTISLACNDMTPEQMATNVNCSSPERHTRSYDYME

GGDIRVRRLFCRTQWYLRIDKRGKVKGTQEMKNNYNIMEIRTVAVGIVAIKGVESEFYL

AMNKEGKLYAKKECNEDCNFKELILENHYNTYASAKWTHNGGEMFVALNQKGIPVRG

KKTKKEQKTAHFLPMAIT;

FGF8_HUMAN Fibroblast growth factor 8 - Homo sapiens (Human).
MGSPRSALSCLLLHLLVLCLQAQEGPGRGPALGRELASLFRAGREPQGVSQQHVREQSL

VTDQLSRRLIRTYQLYSRTSGKHVQVLANKRINAMAEDGDPFAKLIVETDTFGSRVRVR

GAETGLYICMNKKGKLIAKSNGKGKDCVFTEIVLENNYTALQNAKYEGWYMAFTRKG

RPRKGSKTRQHQREVHFMKRLPRGHHTTEQSLRFEFLNYPPFTRSLRGSQRTWAPEPR;

FGF9_HUMAN Glia-activating factor - Homo sapiens (Human).
MAPLGEVGNYFGVQDAVPFGNVPVLPVDSPVLLSDHLGQSEAGGLPRGPAVTDLDHLK

GILRRRQLYCRTGFHLEIFPNGTIQGTRKDHSRFGILEFISIAVGLVSIRGVDSGLYLGMNE

KGELYGSEKLTQECVFREQFEENWYNTYSSNLYKHVDTGRRYYVALNKDGTPREGTRT

KRHQKFTHFLPRPVDPDKVPELYKDILSQS;

FGF10_HUMAN Fibroblast growth factor 10 - Homo sapiens (Human).
MWKWILTHCASAFPHLPGCCCCCFLLLFLVSSVPVTCQALGQDMVSPEATNSSSSSFSSP

SSAGRHVRSYNHLQGDVRWRKLFSFTKYFLKIEKNGKVSGTKKENCPYSILEITSVEIGV

VAVKAINSNYYLAMNKKGKLYGSKEFNNDCKLKERIEENGYNTYASFNWQHNGRQM

YVALNGKGAPRRGQKTRRKNTSAHFLPMVVHS;

FGF11_HUMAN Fibroblast growth factor 11 - Homo sapiens (Human).
MAALASSLIRQKREVREPGGSRPVSAQRRVCPRGTKSLCQKQLLILLSKVRLCGGRPARP

DRGPEPQLKGIVTKLFCRQGFYLQANPDGSIQGTPEDTSSFTHFNLIPVGLRVVTIQSAKL

GHYMAMNAEGLLYSSPHFTAECRFKECVFENYYVLYASALYRQRRSGRAWYLGLDKE

GQVMKGNRVKKTKAAAHFLPKLLEVAMYQEPSLHSVPEASPSSPPAP;

FGF12_HUMAN Fibroblast growth factor 12 - Homo sapiens (Human).
MAAAIASSLIRQKRQARESNSDRVSASKRRSSPSKDGRSLCERHVLGVFSKVRFCSGRKR

PVRRRPEPQLKGIVTRLFSQQGYFLQMHPDGTIDGTKDENSDYTLFNLIPVGLRVVAIQG

VKASLYVAMNGEGYLYSSDVFTPECKFKESVFENYYVIYSSTLYRQQESGRAWFLGLN

KEGQIMKGNRVKKTKPSSHFVPKPIEVCMYREPSLHEIGEKQGRSRKSSGTPTMNGGKV

VNQDST;

FGF13_HUMAN Fibroblast growth factor 13 - Homo sapiens (Human).
MAAAIASSLIRQKRQAREREKSNACKCVSSPSKGKTSCDKNKLNVFSRVKLFGSKKRRR

RRPEPQLKGIVTKLYSRQGYHLQLQADGTIDGTKDEDSTYTLFNLIPVGLRVVAIQGVQT

KLYLAMNSEGYLYTSELFTPECKFKESVFENYYVTYSSMIYRQQQSGRGWYLGLNKEG

EIMKGNHVKKNKPAAHFLPKPLKVAMYKEPSLHDLTEFSRSGSGTPTKSRSVSGVLNGG

KSMSHNEST;

FGF14_HUMAN Fibroblast growth factor 14 - Homo sapiens (Human).
MAAAIASGLIRQKRQAREQHWDRPSASRRRSSPSKNRGLCNGNLVDIFSKVRIFGLKKR

RLRRQDPQLKGIVTRLYCRQGYYLQMHPDGALDGTKDDSTNSTLFNLIPVGLRVVAIQG

VKTGLYIAMNGEGYLYPSELFTPECKFKESVFENYYVIYSSMLYRQQESGRAWFLGLNK

EGQAMKGNRVKKTKPAAHFLPKPLEVAMYREPSLHDVGETVPKPGVTPSKSTSASAIM

NGGKPVNKSKTT;

-continued

FGF15_MOUSE Fibroblast growth factor 15 - *Mus musculus* (Mouse).
MARKWNGRAVARALVLATLWLAVSGRPLAQQSQSVSDEDPLFLYGWGKITRLQYLYS

AGPYVSNCFLRIRSDGSVDCEEDQNERNLLEFRAVALKTIAIKDVSSVRYLCMSADGKIY

GLIRYSEEDCTFREEMDCLGYNQYRSMKHHLHIIFIQAKPREQLQDQKPSNFIPVFHRSFF

ETGDQLRSKMFSLPLESDSMDPFRMVEDVDHLVKSPSFQK;

FGF16_HUMAN Fibroblast growth factor 16 - *Homo sapiens* (Human).
MAEVGGVFASLDWDLHGFSSSLGNVPLADSPGFLNERLGQIEGKLQRGSPTDFAHLKGI

LRRRQLYCRTGFHLEIFPNGTVHGTRHDHSRFGILEFISLAVGLISIRGVDSGLYLGMNER

GELYGSKKLTRECVFREQFEENWYNTYASTLYKHSDSERQYYVALNKDGSPREGYRTK

RHQKFTHFLPRPVDPSKLPSMSRDLFHYR;

FGF17_HUMAN Fibroblast growth factor 17 - *Homo sapiens* (Human).
MGAARLLPNLTLCLQLLILCCQTQGENHPSPNFNQYVRDQGAMTDQLSRRQIREYQLYS

RTSGKHVQVTGRRISATAEDGNKFAKLIVETDTFGSRVRIKGAESEKYICMNKRGKLIGK

PSGKSKDCVFTEIVLENNYTAFQNARHEGWFMAFTRQGRPRQASRSRQNQREAHFIKRL

YQGQLPFPNHAEKQKQFEFVGSAPTRRTKRTRRPQPLT;

FGF18_HUMAN Fibroblast growth factor 18 - *Homo sapiens* (Human).
MYSAPSACTCLCLHFLLLCFQVQVLVAEENVDFRIHVENQTRARDDVSRKQLRLYQLY

SRTSGKHIQVLGRRISARGEDGDKYAQLLVETDTFGSQVRIKGKETEFYLCMNRKGKLV

GKPDGTSKECVFIEKVLENNYTALMSAKYSGWYVGFTKKGRPRKGPKTRENQQDVHF

MKRYPKGQPELQKPFKYTTVTKRSRRIRPTHPA;

FGF19_HUMAN Fibroblast growth factor 19 - *Homo sapiens* (Human).
MRSGCVVVHVWILAGLWLAVAGRPLAFSDAGPHVHYGWGDPIRLRHLYTSGPHGLSS

CFLRIRADGVVDCARGQSAHSLLEIKAVALRTVAIKGVHSVRYLCMGADGKMQGLLQY

SEEDCAFEEEIRPDGYNVYRSEKHRLPVSLSSAKQRQLYKNRGFLPLSHFLPMLPMVPEE

PEDLRGHLESDMFSSPLETDSMDPFGLVTGLEAVRSPSFEK;

FGF20_HUMAN Fibroblast growth factor 20 - *Homo sapiens* (Human).
MAPLAEVGGFLGGLEGLGQQVGSHFLLPPAGERPPLLGERRSAAERSARGGPGAAQLA

HLHGILRRRQLYCRTGFHLQILPDGSVQGTRQDHSLFGILEFISVAVGLVSIRGVDSGLYL

GMNDKGELYGSEKLTSECIFREQFEENWYNTYSSNIYKHGDTGRRYFVALNKDGTPRD

GARSKRHQKFTHFLPRPVDPERVPELYKDLLMYT;

FGF21_HUMAN Fibroblast growth factor 21 - *Homo sapiens* (Human).
MDSDETGFEHSGLWVSVLAGLLLGACQAHPIPDSSPLLQFGGQVRQRYLYTDDAQQTE

AHLEIREDGTVGGAADQSPESLLQLKALKPGVIQILGVKTSRFLCQRPDGALYGSLHFDP

EACSFRELLLEDGYNVYQSEAHGLPLHLPGNKSPHRDPAPRGPARFLPLPGLPPALPEPP

GILAPQPPDVGSSDPLSMVGPSQGRSPSYAS

FGF22_HUMAN Fibroblast growth factor 22 - *Homo sapiens* (Human).
MRRRLWLGLAWLLLARAPDAAGTPSASRGPRSYPHLEGDVRWRRLFSSTHFFLRVDPG

GRVQGTRWRHGQDSILEIRSVHVGVVVIKAVSSGFYVAMNRRGRLYGSRLYTVDCRFR

ERIEENGHNTYASQRWRRRGQPMFLALDRRGGPRPGGRTRRYHLSAHFLPVLVS;
and

FGF23_HUMAN Fibroblast growth factor 23 - *Homo sapiens* (Human).
MLGARLRLWVCALCSVCSMSVLRAYPNASPLLGSSWGGLIHLYTATARNSYHLQIHKN

GHVDGAPHQTIYSALMIRSEDAGFVVITGVMSRRYLCMDFRGNIFGSHYFDPENCRFQH

QTLENGYDVYHSPQYHFLVSLGRAKRAFLPGMNPPPYSQFLSRRNEIPLIHFNTPIPRRHT

RSAEDDSERDPLNVLKPRARMTPAPASCSQELPSAEDNSPMASDPLGVVRGGRVNTHA

GGTGPEGCRPFAKFI.

FGF homologous factors (FHF) can also function as FGF since they share substantial sequence homology as FGF. Kaposi's sarcoma cells secrete a homologue of FGF (FHF) called the K-FGF proto-oncogene. Additional FHFs are FHF1-FHF4, which are also known as FGF11-FGF14. Pairwise comparisons between the FHF1-FHF4 show between 58% and 71% amino acid sequence identity, but each FHF shows less than 30% identity when compared with other FGFs Amounts or concentrations of FGF appropriate in media formulations of the invention are from about 1 to about 500 ng/ml. Additional non-limiting examples of amounts or concentrations of FGF appropriate in media formulations of the invention are from about 5 to about 100 ng/ml, 5 to about 50 ng/ml, 10 to about 20 ng/ml.

FGF2 is susceptible to degradation by repeated freeze/thaw cycles or exposure to plastic, filters and similar surfaces. FGF is typically stored at about −20° C. or less, with a carrier protein (for example albumin) at concentrations greater than 1 mg/ml total protein. FGF can be stored as a liquid at 4° C. for up to about a week or so. FGF biological activity decreases with time in a cell culture media—for example, after 24 hours in culture media, FGF2 activity decreases significantly. FGF is typically added to media alone or in combination with a fresh media to cultured cells when cells are fed.

FGF can be provided by feeder cells. Feeder cells produce FGF, which in turn can be added as a component of a media formulation of the invention. Thus, FGF in media can comprise FGF without feeder cells or FGF producing feeder cells, such as FGF feeder cells in a cell culture that includes a media formulation of the invention. Thus, a media formulation of the invention may or may not include cells that produce FGF, referred to as FGF feeder cells. FGF feeder cells are usually a mixture or derived from fibroblastic or connective tissue. Specific non-limiting examples of feeder cells include embryonic fibroblasts (human or other species—rodent, for example) and fetal fibroblasts (from fetal annexes resulting at birth—placenta, umbilical cord, for example). Specific examples of feeder cells also include adult tissue, such as skin (foreskin) and peritoneum (resulting from excisions of hernial sacs). Specific non-limiting examples of established feeder cell lines include, for example, immortalized BJ-TERT fibroblasts, CHO and STO cell lines.

Media formulations of the invention can include, for example, salts or minerals. Minerals and salts include, for example, sodium, potassium, calcium, magnesium, copper, manganese, molybdenum, selenium, silicon, iron, zinc, vanadium, boron, cobalt, iodine, chromium and tin. Minerals or salts can be provided as organic (organic acids) or inorganic salts (e.g., chlorides, sulfates, phosphates or nitrates). In a non-limiting example, a selenium salt is sodium selenite.

Amounts or concentrations of minerals or salts will depend upon the particular mineral or salt. A particular non-limiting example for sodium is a concentration of about 130-160 mg/Liter. A particular non-limiting example for potassium is a concentration of 3 to 6 mg/Liter. A particular non-limiting example for calcium is a concentration of 7 to 12 mg/Liter. A particular non-limiting example for magnesium is a concentration of 1 to 4 mg/deciliter. For trace elements such as copper, manganese, molybdenum, selenium, iron, or zinc, a non-limiting concentration is about 1 pg/deciliter to 1 ug/deciliter. Mineral and salt solutions are stable and therefore can be stored at room temperature, refrigerated or frozen if desired.

Media formulations of the invention can include, for example, essential amino acids. Essential amino acids include, for example, arginine; cystine; histidine; isoleucine; leucine; methionine; phenylalanine; threonine; tryptophan; tyrosine; and valine.

Amounts or concentrations of essential amino acids can vary and may depend in part upon the particular amino acid. An amount or concentration of an essential amino acid appropriate in media formulations of the invention is about 0.5 to 10 mmol/Liter. A more particular non-limiting amount or concentration is about 2.5 nmol/Liter. Amino acid solutions are stable and can be stored at 4° C. Amino acid solutions should be protected from light.

Media formulations of the invention typically have an osmolarity such that when the media is in contact with the cells, the osmolarity will be compatible with cell survival or proliferation. Exemplary osmolarity for a liquid media formulation can range from about 240-300 mOsm/Liter, or from about 250-270 mOsm/Liter.

Osmolarity is measure of osmoles of solute per litre of solution. Media osmolarity can be measured by various methods including freezing-point depression osmometry (using the variations in the freezing temperature of the aqueous liquids at different osmotic pressures), vapor pressure osmometry (determine the concentration of osmotically active particles that reduce the vapor pressure of a solution) and oncometry using a semipermeable membrane and a reference solution to measure the oncotic pressure (given by large molecules—for example proteins, carbohydrates). Commercially available osmometers can accurate measure osmolarity between 0 and 4000 mOsm/KgH$_2$O.

Media formulations of the invention can include, for example, globulins. Globulins play a role in various functions, such as transporting fatty acids, thyroid and steroid hormones and other substances. Globulins also contribute to maintaining osmotic pressure of extracellular fluid. Non-limiting examples of globulins include alpha-, beta- and gamma-globulin and antibodies (e.g. IgG, IgA, IgM, IgE and IgD). Globulins can be mammalian, such as primate (e.g., human) or ungulate (e.g., bovine, goat, equine or porcine).

Amounts or concentrations of globulins appropriate in media formulations of the invention are from about 0.1 to about 25 g/L. Additional non-limiting examples of amounts or concentrations of globulin appropriate in media formulations of the invention are from about 0.5 to about 20 g/L, 1 to about 10 g/L, or 1 to about 5 g/L. As with albumins, globulins are susceptible to pH below 6, exposure to light and temperatures that cause protein denaturation. Globulin stock solutions can be stored at −20° C. Concentrated globulin solutions of 10-40% can be frozen for long periods of time.

Relative concentration ratios of globulin to albumin appropriate in media formulations of the invention are about 1:2, or less than about 1:2. Additional non-limiting examples of concentration ratios of globulin to albumin appropriate in media formulations of the invention are from about 1:0.5, 1:0.75, 1:1, 1:1.5, 1:2.5, or 1:3.

The synthesis of HA occurs in membrane structures. HA, with different levels of polymerization (or fragmentation), may have various effects on cell survival, proliferation, adhesion or migration. Although not wishing to be bound by theory, CD44 is the major receptor for HA and a ubiquitous membrane protein with multiple functions. After binding to CD44, HA could form a surrounding capsule with beneficial or detrimental effects on the cell biology. For example, encapsulating a more complex structure of a blastocyst could be beneficial by creating a trap for the autocrine secretion of the trophoblast or by creating a protection envelope for the embryo up to the stage of hatching and implantation. In this regard, the concentration of HA is a good indicator of the viability, maturation and implantation of the blastocyst. The HA concentration is 0.05 to 3 mg/ml in the adult tissue, in the cumulus ooforus complex is 0.5-1 mg/ml, and about 50 ng/ml in the follicular fluid.

Media formulations of the invention can include, for example, a glycosaminoglycan or a glycosaminoglycan degradation product. In various embodiments, glycosaminoglycans or fragments of glycosaminoglycans, such as HA, can be used as a supplement in addition to a glycosidase or hydrolase in a media formulation of the invention, or can be used in place of a glycosidase or hydrolase in a media formulation of the invention.

Glycosaminoglycan degradation products can be produced by glycosidases or hydrolases. A non-limiting example of a glycosaminoglycan degradation product is a degradation product of hyaluronic acid (HA). Additional non-limiting examples of a glycosaminoglycan degradation product is a degradation product of chondroitin, chondroitin sulfate or a mucin (e.g., mucin1, mucin2, mucin3, mucin4, mucin5AC, mucin5B, mucin6, mucin7, mucin8 or mucin9). Glycosaminoglycan degradation products include, for example, di-, tri-, tetra-, penta-, hexa-, hepta-, octa-saccharide, or larger saccharide polymers.

Media formulations of the invention therefore can include one or more supplements. A supplement refers to a component or ingredient that can be added to a complete or incomplete media formulation. Thus, a supplement of an incomplete media formulation can be a component of a complete media. For example, where an incomplete media lacks albumin, a supplement can be albumin which, when added to the incomplete media results in a complete media. Similarly, where an incomplete media lacks an iron carrier, glutamine, a glyocidase or hydrolase, FGF, a salt or mineral or essential amino acids, a supplement for each such incomplete media could be, respectively, an iron carrier, glutamine, a glyocidase or hydrolase, FGF, a salt or mineral and essential amino acids.

Additional specific non-limiting examples of supplements include energy sources such as mono- or poly-saccharides (e.g., glucose or pyruvate); non-essential amino acids (e.g., alanine, asparagine, aspartate, glycine, proline or serine); hormones (e.g., insulin, insulin-like growth factor, a thyroid hormone such as thyroxine (T4) or triiodothyronine (T3), or a progesterone); cytokines and growth factors (e.g. epidermal growth factor (EGF), keratinocyte growth factor (KGF), hepatocyte growth factor (HGF), insulin like growth factor-1 and -2 (IGF-1, IGF-2), nerve growth factor (NGF)); interleukins and interferons; vitamins (e.g., A, $B_1$, $B_2$, $B_6$ $B_{12}$, C, D, E, K, biotin); heparin, heparin sulfate, buffers or salts (e.g., Earle's salts, Hanks' salts, Puck's salts, etc.), glycosaminoglycan degradation products, and co-factors. Additional supplements include, for example, β-mercaptoethanol, Leukemia Inhibitory Factor (LIF, ESGRO™), or serum substitutes, such as KNOCKOUT SR, an FBS substitute for stem cell culture media.

Supplements also include, for example, animal sera, such as bovine sera (e.g., fetal bovine, newborn calf or normal calf sera), human sera, equine sera, porcine sera, monkey sera, or ape sera, typically at a concentration of about 1-25% (e.g., about 5-15% or about 10%); attachment factors or extracellular matrix components, such as collagens, laminins, proteoglycans, fibronectin, and vitronectin; and lipids, such as phospholipids, cholesterol, fatty acids, and sphingolipids.

Amounts or concentrations of these and other supplements are typically determined by the particular media, growth conditions and cell types cultured in the media. For glucose, a particular concentration is about 10 to 1000 mg/Liter. For insulin or insulin-like growth factor a particular concentration is between about 5 to 40 ug/ml. For a thyroid hormone such as thyroxine (T4) or triiodothyronine (T3) a particular concentration is between about 1 to 40 ng/ml.

Media formulations of the invention can include, for example, anti-microbials. Anti-microbials are any an anti-bacterial (cidal or static), e.g., gram positive or gram negative, anti-viral (cidal or static), anti-mycoplasma (cidal or static) or anti-fungal (cidal or static) molecule. Specific non-limiting examples include antibiotics such as ampicillin, penicillin, geneticin, streptomycin, kanamycin, gentamycin; and anti-fungals such as mycostatin (Nystatin) and amphotercin B (Fungizone).

Media formulations of the invention can include, for example, a substrate. Substrates include adhesion molecules useful for cell attachment. Non-limiting examples of adhesion molecules include one or more of laminin or fibronectin. An additional non-limiting example of an adhesion molecule is a proteoglycan, such as hyaluronic acid, chondroitin, chondroitin sulfate or a mucin (e.g., mucin1, mucin2, mucin3, mucin4, mucin5AC, mucin5B, mucin6, mucin7, mucin8 or mucin9).

Media formulations of the invention when used for sustaining or maintaining cells are typically pH stabilized or buffered. Exemplary buffers are bicarbonate, phosphate ethanolamine, triethanolamine (Tris), trometamol and HEPES based buffers.

Exemplary media formulations of the invention, when in a liquid form, are in the physiological pH range. Physiologic pH is typically greater than about 4 and less than about 9. Other exemplary pH ranges are about 4.0 to 5.0, 5.0 to 6.0, 6.0 to 7.0, 7.0 to 8.0, 8.0 to 9.0. Non-limiting particular examples are a pH between about 7.0-7.8, when present in a 2-20% oxygen environment, a 5-15% carbon dioxide environment, or a normal atmospheric environment (e.g., atmospheric carbon dioxide concentration is between about 0.03 and 0.06% and normal atmospheric oxygen concentration is about 20%).

Complete and incomplete media formulations can be a liquid, solution, suspension, powder, tablet, capsule, crystals, granules, cake, paste, lyophilized or freeze-dried. The powder, tablet, capsule, crystals, granules, cake, paste, lyophilized or freeze-dried forms can be reconstituted by mixing in liquid to produce a reconstituted liquid, e.g., a liquid media formulation. Powdered media typically have a longer shelf live than liquid media Liquid culture media can be provided ready-to-use or require supplementation with one or more components or ingredients prior to use, if desired, and the formulation can be optimized for particular cell types. Liquid media may be supplemented prior to packaging, shipment or use in a cell culture with more labile components to produce a media formulation of the invention. For example, glutamine, transferrin, albumin, FGF, a glycosidase or hydrolase (e.g., hyaluronidase), globulin, serum (calf), amino acids (e.g., glutamine), transferrin, hormones (e.g., progesterone, insulin, thyroid hormones), cytokines, growth factors, and lipids (e.g., phospholipids, fatty acids) are all at least somewhat labile and may added as supplements to liquid media.

Liquid or powder complete or incomplete media formulations may be stored at temperatures below ambient temperature in order to inhibit degradation of media components or ingredients. Supplements for addition to complete or incomplete media formulations may also be stored at temperatures below ambient temperature in order to inhibit degradation. Such temperatures include refrigeration (e.g., from about 0-18° C.) to or freezing (e.g., about 0° C. or less, for example, −20° C., or less).

Non-liquid (e.g., powdered) media formulations are typically produced by admixing dried individual components or sets of components in amounts or concentrations according to the media formulations set forth herein, via a mixing process, e.g., ball-milling (also referred to as Fitzmilling), or by lyophilizing/freeze-drying a liquid culture media. Such non-processed powders often produce dust when used, or dissolve poorly or slowly in liquid. Powdered media formulations can therefore be prepared using fluid bed technology (i.e., "agglomeration"), via tumble granulation, or spray-drying. Agglomerated or spray-dried powders are substantially dust-free or dissolve rapidly.

Fluid bed technology is a process of producing agglomerated powders having altered characteristics (particularly, for example, solubility) from the starting materials. In brief, powders are suspended in an upwardly moving column of a gas (e.g., atmospheric air or an inert gas such as nitrogen) while at the same time a controlled and defined amount of liquid is injected into the powder stream to produce a moistened powder. The volume of liquid introduced into the dry powder will depend at least in part upon the mass of media to be agglomerated. Typical volumes of solvent, per 500 grams of media, are about 5-100 ml, or about 10-50 ml, or about 25-50 ml (e.g., about 35 ml). Liquid introduction rates, per 500 grams of media, are a rate of about 1-10 ml/min, or about 2-8 ml/min, or about 4-8 m/min (e.g., about 6 ml/min). In some situations, it may be desirable to cycle between adding liquid for a period of time (e.g., about 1 minute) and then not adding liquid for a period of time (e.g., about 1 minute), so as to inhibit clumping of the powder during agglomeration. Mild heat is then used to dry the material, producing an agglomerated powder. Typical temperatures for drying of agglomerated powder are about 50-80° C., or about 55-75° C., or about 60-65° C. Powder is typically dried in about 3-10 minutes (e.g., for about 5-7 minutes), per 500 grams of powder.

Apparatuses for producing or processing materials by fluid bed technology are available commercially (e.g., from Niro, Inc., Columbia, Md.). Such apparatuses have been used to prepare agglomerated powders of various materials.

Powdered media formulations can also be produced by tumble granulation, which also produces an agglomerated material. In such a process, dry powder media is introduced into a tumble granulator or a tumble blender such as those commercially available from Gemco (Middlesex, N.J.) and Patterson Kelley (East Stroudsburg, Pa.). A liquid (e.g., water, buffered saline, or other solvent) is introduced into the powder under controlled conditions in the tumble granulator and the batch is then dried according to the manufacturer's specifications to form a granulated powder media formulation.

Powdered media formulations can additionally be produced by spray-drying. Media in a liquid form is placed into a spray-drying apparatus and are then converted into a corresponding powder by spraying the solution into a chamber in the apparatus under appropriate conditions to produce the powders, such as under controlled temperature and humidity, until powder is formed.

In a typical spray-drying approach, a liquid media is aspirated into the apparatus and atomized into a spray with a rotary- or nozzle-type atomizer. The atomized spray is then mixed with a gas (e.g., nitrogen or air) and sprayed into a drying chamber under conditions that promote production of a powdered product. Typical spray conditions are a spray rate of about 25-100 g/min, or about 30-90 g/min, 35-85 g/min, 40-80 g/min, 45-75 g/min, 50-75 g/min, 55-70 g/min, or 60-65 g/min, or about 65 g/min. Typical inlet air temperatures in the atomizer is about 100-300° C., or about 150-250° C., or about 200° C., with a typical outlet temperature of about 50-100° C. or about 60-80° C., or about 70° C. Air flow in the atomizer is typically set at about 50-100 kg/hr, or about 75-90 kg/hr, or about 80.0 kg/hr, at a nozzle pressure of about 1-5 bar, or about 2-3 bar, or about 2.0 bar. Under such conditions, the solvent in the liquid evaporates in a controlled manner, thereby forming free-flowing particles (i.e., powder). Following drying, the powder is discharged from the drying chamber, passed through one or more filters and collected for further processing (e.g., sterilization, packaging, etc.).

Apparatuses for producing particulate materials by spray-drying are commercially available (e.g., from Niro, Inc., Columbia, Md.). According to the manufacturer, these apparatuses have been used to prepare powders of various materials.

The resulting powdered media may then be dissolved in a reconstituting volume of liquid with or without further supplementation. Such media can be reconstituted under sterile conditions and, following reconstitution, be stored at temperatures below ambient temperature (e.g., 4 to 10° C.). As with liquid media, for a powdered media, one or more labile components may be added at subsequent time point to the powder, for example, prior to sterilization, packaging, shipment or use in a cell culture. Thus, such mixing and processing of media may occur with incomplete media or less than all of the components of complete media and therefore, prior to all components or ingredients being present in a complete media formulation of the invention.

Liquids suitable for media include solvents or solutions compatible with the media formulation. The term "compatible," when used in reference to a liquid for a media formulation means that the solvent or solution does not induce irreversible deleterious changes in the performance characteristics of the media, such as breakdown or aggregation of the components or ingredients of the media formulation or destroying the compatibility of media with cell survival or proliferation. Non-limiting examples of suitable solvents are water (e.g., distilled or deionized water), embryo tested water (e.g., Sigma-Aldrich), aqueous buffer solutions and serum (e.g., bovine, such as fetal bovine serum or calf serum or human serum).

One or more components or ingredients of a complete or incomplete media formulation may be included in the liquid solvent used for dissolving a powdered media. One or more supplements may be included in the liquid solvent used for dissolving a powdered media.

Media formulations that are included in the invention include, but not limited to, DMEM, MEM, F-12, RPMI-1640, MDEM, M199, IDMM, MCDB (105, 131), M199 McCoy's 5A, Williams' media, Lebovitz's L-15, and combinations thereof (e.g., DMEM:F-12). Media formulations that are also included in the invention include KO (knockout) media, which lack a particular component or ingredient. These formulations, and components and ingredients for producing the media formulations of the invention, are available commercially (e.g., Sigma-Aldrich, St Louis Mo.; Chemicon, Temecula, Calif.; Invitrogen, Carlsbad, Calif.) or can be obtained using methods known in the art.

Components that make up the complete and incomplete media formulations may but are not required to be purified. The term "purified" used as a modifier of a composition, such as a media formulation component, refers to a composition free of most or substantially all of the materials with which it typically associates with in nature. For example, purified albumin is typically removed from components normally present in the serum milieu. Purified does not require absolute purity and is context specific. Furthermore, a "purified" composition can be combined with one or more other molecules, such as components of a media formulation. Thus, the term "purified" does not exclude combinations of purified components.

Typically, media formulations are sterilized so as to inhibit or prevent microbial growth. Sterilization methods include gamma or ultraviolet irradiation; liquid media is often sterilized by filtration, and powdered media can be sterilized by ethylene oxide permeation after formulation. Total doses of gamma irradiation are typically about 10-100 kilograys (kGy), or about 15-75 kGy, 15-50 kGy, 15-40 kGy or 20-40 kGy, or a total dosage of about 20-30 kGy, or about 25 kGy, for about 1 hour to about 7 days, or about 1 hour to about 5 days, 1 hour to about 3 days, about 1-24 hours or about 1-5 hours, or about 1-3 hours. A slow dose of gamma irradiation is a total dosage of about 25-100 kGy over a period of about 1-5 days. During irradiation, the media can be stored at a temperature of about −70° C. to about room temperature (about 20-25° C.), or about −70° C. Of course, radiation dose and exposure times can be adjusted according to bulk or mass of the irradiated material. Media formulations may be sterilized prior to or following packaging, for example, in a kit or container.

Complete media formulations, compositions and preparations and components therein are generally described herein in terms of amounts to be used for cell culture, which can be referred to as a "1× media formulation" or a "working concentration" or "working amount." A 1× complete media formulation or a working amount is that which is appropriate for sustaining or maintaining cell viability, survival or proliferation of a cell culture.

Media formulations, compositions and preparations also include concentrated and diluted forms. When the concentrated media is diluted the media can maintain cell viability, and when diluted forms concentrated the media can maintain cell viability. Thus, invention media formulations include concentrated and diluted media formulations. Such concentrated and diluted media may be diluted or concentrated, as appropriate, to working concentrations or amounts prior to use. Exemplary concentrated forms of a media formulation, media composition or media preparation are 5×, 10×, 20×, 50×, 100×, 150×, 200× or more concentrated, which means that the components therein are at 5-, 10-, 20-, 50-, 100-, 150-, 200-fold concentration, as compared to a 1× media formulation. Thus, for example, a 5× media formulation, when diluted to 1× media formulation, can maintain or sustain cell viability for an amount of time. Exemplary diluted forms of a media formulation, media composition or media preparation are 0.75×, 0.5×, 0.25×, 0.10× or more diluted, which means that the components therein are at 0.75-, 0.5-, 0.25-, 0.10-fold concentration, as compared to a 1× media formulation. Thus, for example, a 0.75× media formulation, when concentrated to a 1× media formulation, can maintain or sustain cell viability for an amount of time.

The invention also provides methods of producing media formulations. In one embodiment, a method includes combining the following components: albumin, an iron carrier, glutamine, a glycosidase or hydrolase, fibroblast growth factor (FGF), a salt or mineral, and essential amino acids. In another embodiment, a method includes combining the following components: albumin, an iron carrier, glutamine, a glycosaminoglycan degradation product, fibroblast growth factor (FGF), a salt or mineral, and essential amino acids. Such components can added individually or in combination with each other. For example, albumin can be combined with an iron carrier, glutamine, a glycosidase or hydrolase, fibroblast growth factor (FGF), a salt or mineral, and essential amino acids; or albumin and glutamine combined together can be combined with an iron carrier, a glycosidase or hydrolase, fibroblast growth factor (FGF), a salt or mineral, and essential amino acids. In particular aspects, the media formulation produced is a liquid having an osmolarity of about 220-330 mOsm/Liter.

Complete and incomplete media formulations can be included or packaged in kits or containers, the kits or containers optionally including instructions for maintaining survival or proliferation of cells. Specific non-limiting examples of kits and containers include a complete media formulation of the invention, with instructions for maintaining survival or proliferation of stem cells without substantial differentiation.

A kit or container typically has "packaging material," which refers to a physical structure housing a component(s) of the kit or container. The packaging material can maintain or be suitable to maintain media or components sterilely, and can be made of material commonly used for such purposes. A kit or container can include a label or packaging insert with appropriate instructions, for example. The instructions may be on "printed matter," e.g., on paper or cardboard within the kit or container, or on a label affixed to the kit or container. Instructions may comprise audio or video medium and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Specific non-limiting examples of kits and containers include containers suitable for a liquid, such as bottles, flasks, jars, vials, tubes, and ampules. Materials suitable for bottles, flasks, jars, vials, tubes, and ampules include glass or a polyolefin. Exemplary polyolefins include, or example, polystyrene, polypropylene, polyethylene, and polybutylene. Additional specific non-limiting examples of kits and containers include pouches, boxes, cartons and drums. Such kits and containers include a packaging material suitable for a volume of media of about 100-250 ml, 250-500 ml, or 500-1000 ml.

Kits and containers may be vacuum sealed or packaged. One example is a "brick-pack" in which the media is packaged into a flexible container, such as a bag or a pouch, which is sealed while being evacuated. Such packages may include one or more access ports (such as valves, luer-locks, etc.) to allow introduction of a liquid (e.g., water, embryo tested water, sera, media or other solvent or solution) into the package to facilitate dissolving or resuspending the media.

Kits and containers may include multiple (two or more) units of a complete media formulation of the invention. Kits and containers may also include an incomplete media formulation lacking one or more components, with the one or more components packaged separately from the incomplete media. Thus, a kit or container may contain 1) an incomplete media and; 2) components packaged separately, so that when the components are combined with the incomplete media a complete media formulation is produced (e.g., a complete media formulation having an osmolarity of about 220-330 mOsm/Liter). In a particular non-limiting example, a kit or container can include a first and second container, the first container including therein a media formulation comprising the following components: an iron carrier, a salt or mineral, and essential amino acids; and a second container, said the second container including therein the following components: albumin, glutamine, a glycosidase or hydrolase, and fibroblast growth factor (FGF).). In another particular non-limiting example, a kit or container can include one more packages that contain albumin, an iron carrier; glutamine; a glycosidase or hydrolase, fibroblast growth factor (FGF), a salt or mineral, and essential amino acids, in individual packages or together in packages (e.g., a salt or mineral and essential amino acids combined in an individual package).

Complete media formulations include media formulations with cells in culture. The invention therefore provides cell cultures that include media formulations of the invention. In such embodiments, cultured cells are contacted with a complete media formulation of the invention under conditions, such as controlled temperature, humidity, and atmosphere, favoring survival or proliferation of the cells. Contact occurs for a period of time, typically at least 10 or more minutes, or greater than 20 minutes, for example, 30, 60, 90, 120, 240 minutes, or more (e.g., 1, 2, 3, 4, 5, 6, 7, 8, 20, 23, 26, 30, 34, 36 or 48 hours or more).

The term "cell culture" refers to cells sustained, maintained, grown or proliferated (expanded) in an in vitro or artificial environment. A "cell culture" is a generic term that can also be used to encompass individual clonal cells, but also groups of cells, progenitor cells, differentiated and non-differentiated cells and mixtures thereof.

Cells that are amenable to cell culture include, but are not limited mammalian cells, including somatic, a germ, a normal, diseased, transformed, mutant, animal cells, including primary isolates, secondary or further passaged cells, and immortalized mammalian (e.g., human) cells. Cells may be anchorage-dependent or anchorage-independent (i.e., "suspension") cells. A non-limiting example of a class of mammalian cells is a stem cell, such as an embryonic, tissue specific, germinal or adult stem cell. Stem cells include totipotent, pluripotent and multipotent stem cells. Another non-limiting example of a class of mammalian cells are tumor or cancer cells, such as breast, prostate, haematopoietic, stomach, colon, lung, pancreas, bladder, kidney, brain (e.g., glioma). Additional particular examples of mammalian cells include but are not limited to CHO cells, COS cells, VERO cells, HEK cells, BHK cells, hybridoma cells, STO cells, BJ-TERT fibroblasts and HeLa cells.

Totipotent stem cells can give rise to all cell types found in an embryo, fetus, or developed organism, including the embryonic components of the trophoblast and placenta required to support development and birth. The zygote and the cells at the very early stages following fertilization (i.e., the 2-cell stage) are considered totipotent.

Pluripotent stem cells are somewhat less plastic in their differentiative capacity than totipotent stem cells, but can become all cell types that are found in an implanted embryo, fetus, or developed organism. Unlike totipotent stem cells, pluripotent stem cells do not form embryonic components of the trophoblast or placenta.

A multipotent stem cell is a progeny of a stem cell within a particular tissue, organ, or physiological system that is able to divide for many generations (the number of cell divisions may or may not be limited). Under certain conditions, a multipotent stem cell can give rise to daughter cells (typically, at least one is an undifferentiated cell) a proportion of which eventually terminally differentiates.

Cultures of stem cells typically include a proportion of stem cells capable of differentiation. A proportion of the stem cells in a cell culture may therefore undergo spontaneous differentiation. In a typical healthy population of stem cells, about 80% of the cells are not differentiated and the other 20% may be in various stages of differentiation. In cell cultures in which stem cells are passaged, stem cells as a proportion of the overall cell population can increase in numbers, i.e., proliferate or expand. For example, a starting cell culture in which stem cells comprise a certain percentage of total cells (e.g., 10-20% of the total cells in the culture), stem cells increase in numbers so that the proportion of stem cells in the culture increases (e.g., from 10-20% stem cells to 30, 40, 50, 60, 70, 80% or more stem cells). The invention therefore provides cultured cells, including stem cell cultures, that exhibit proliferation or expansion. In one embodiment, the cultured cells include stem cells that retain pluripotency or proliferate without substantial differentiation, or a majority of stem cells in the culture (e.g., 50%, 60%, 70%, 80% or more remain pluripotent) retain pluripotency or proliferate without substantial differentiation, for one or more passages, e.g., 2, 3, 4, 5 or more passages.

Cell cultures that include media formulations of the invention may include additional supplements, as set forth herein or that would be known to one skilled in the art. Cell cultures that include media formulations of the invention may further include other cells or cell products. A particular non-limiting example of cells is a feeder cell (e.g., FGF producing feeder cells).

Reconstituted media may be used to culture cells. In such techniques, cultured cells are contacted with a reconstituted liquid media formulation under conditions favoring survival or proliferation of the cells.

Methods for culturing cells in media formulations are therefore provided. In one embodiment, a method includes growing or incubating the cells in a complete media formulation of the invention that includes the following components: albumin, an iron carrier, glutamine, a glycosidase or hydrolase, fibroblast growth factor (FGF), a salt or mineral, and essential amino acids, at an osmolarity of about 220-330 mOsm/Liter. In another embodiment, a method includes growing or incubating the cells in a complete media formulation of the invention that includes the following components: albumin, an iron carrier, glutamine, a glycosaminoglycan degradation product, fibroblast growth factor (FGF), a salt or mineral, and essential amino acids, at an osmolarity of about 220-330 mOsm/Liter. In one aspect, the period of time is sufficient to allow cells to proliferate or increase in numbers, for example, by 25%, 50%, 75%, 100% or more. In another aspect, the period of time is for at least about 30, 60, 90, 120, 240 minutes or more, or at least about 1, 2, 3, 4, 5, 6, 7, 8, 10, 12, 16, 20, 24, 36, or 48 hours or more. In additional aspects, cells include stems cells such as embryonic, tissue specific, germinal or adult stem cells; or multipotent, totipotent or pluripotent stem cells. In a further aspect, the stem cells survive or proliferate without substantial differentiation. In yet additional aspects, stem cells, or a majority of stem cells in the culture (e.g., 50%, 60%, 70%, 80% or more) remain pluripotent or proliferate without substantial differentiation, for one or more passages, e.g., 2, 3, 4, 5 or more passages. Methods of culturing cells also include co-cultures, for example, with feeder cells (e.g. FGF or proteoglycan producing feeder cells), as set forth herein or would be known to the skilled artisan.

In methods for culturing stem cells in which stem cells are passaged, stem cells as a proportion of the overall cell population can increase in numbers, i.e., proliferate or expand. The invention therefore includes methods of culturing cells, including stem cells, that result in clonal proliferation or expansion. For example in a starting culture in which stem cells comprise a certain percentage of cells (e.g., 10-20% of total cells), a method of the invention increases numbers of stem cells so that the relative proportion of stem cells in the culture increases over time (e.g., from 10-20% stem cells to 30, 40, 50, 60, 70, 80% or more stem cells). Such methods optionally retain stem cell pluripotency or stem cells proliferate without substantial differentiation for a plurality of passages, e.g., 1, 2, 3, 4, 5 or more passages.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to "a component" includes a plurality of components or ingredients and reference to "a cell" can include a plurality of cells.

As used herein, all numerical values or numerical ranges include whole integers within or encompassing such ranges and fractions of the values or the integers within or encompassing ranges unless the context clearly indicates otherwise. Thus, for example, reference to values such as 25%, 50%, 75%, 100%, includes 25% to 50% (i.e., 25, 26, 27, 28%, etc.), 50 to 75% (50, 51, 52, 53, 54%, etc.), and so forth. In another example, reference to a concentration or amount range of 1 to about 100 g/L includes 1, 2, 3, 4, 5, 6, 7, 8, 9, 10, 11, 12, 13, 14, 15, 16, 17, 18, 19, 20 g/L, etc., as well as 1.1, 1.2, 1.3, 1.4, 1.5 g/L, etc., 2.1, 2.2, 2.3, 2.4, 2.5 g/L, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes studies of 3 passages of stem cells in a media formulation and the effect of hyaluronidase. The media formulation used:

Exemplary Media Formulation: Probumin (Chemicon)—1 to 4 mg/ml; Human Globulins (Sigma-Aldrich)—0.1 to 0.5 mg/ml; Human Transferrin (Sigma Aldrich)—20 ug/ml; Sodium Selenite (Sigma Aldrich), 1 ng/ml; DMEM-F12 1:1, HEPES free (Invitrogen); L-glutamine (or Glutamax) (Invitrogen)—200 uM; MEM non essential amino acid solution NEAA (Invitrogen) 1×; Water for embryo transfer 10 to 20% (Sigma Aldrich); Final osmolarity—250-270 mOsm/L. Media was supplemented before use with FGF2 (Chemicon-Millipore) to a final concentration of 10 ng/ml, and with hyaluronidase to a final concentration of 1 ug/ml.

Exemplary Media Formulation indicated above, without hyaluronidase.

Classic media (conditioned on inactivated mouse fibroblasts): 80% Knockout DMEM (Invitrogen) 20% Knockout Serum Replacement (Invitrogen), supplemented with MEM-Non Essential Aminoacids and L-Glutamine from 100× stock solutions (Invitrogen), beta mercapto-ethanol, 35 ng/mL (Sigma Aldrich) and FGF2, 4 ng/ml final concentration (Chemicon-Millipore). Media was incubated overnight on a confluent culture of inactivated fibroblasts, collected, sterile filtered and supplemented with 10 ng/ml FGF before stem cell culture feeding.

Conditioned media, on inactivated (mitotically inactive) mouse fibroblasts: Same as Exemplary Media Formulation indicated above, except incubated for about 24 hours on a culture of inactivated mouse fibroblasts.

Conditioned classic media with hyaluronidase: 80% Knockout DMEM (Invitrogen) 20% Knockout Serum Replacement (Invitrogen), supplemented with MEM-Non Essential Aminoacids and L-Glutamine from 100× stock solutions (Invitrogen), beta mercapto-ethanol, 35 ng/mL (Sigma Aldrich) and FGF2, 4 ng/ml (Chemicon-Millipore). The media was incubated overnight on a confluent culture of inactivated fibroblasts, collected, sterile filtered and supplemented with 10 ng/ml FGF before stem cell culture feeding. Hyaluronidase was added to a final concentration of 1 ug/ml before use.

Human embryonic stem cells derived from human blastocysts at California Stem Cell Inc., were cultured in 75 cm2 polystyrene flasks at 4×10^6 density using the above described conditions. The flasks were coated with Matrigel 1:30 in base media. Hyaluronidase type 1 purified from bovine testis (Sigma Aldrich) was used. The lyophilized powder was dissolved in sterile distilled water at a concentration of 1 mg/ml and stored frozen at −20° C. Thawed aliquots were kept at 4° C. for maximum 1 week.

Figure 1:
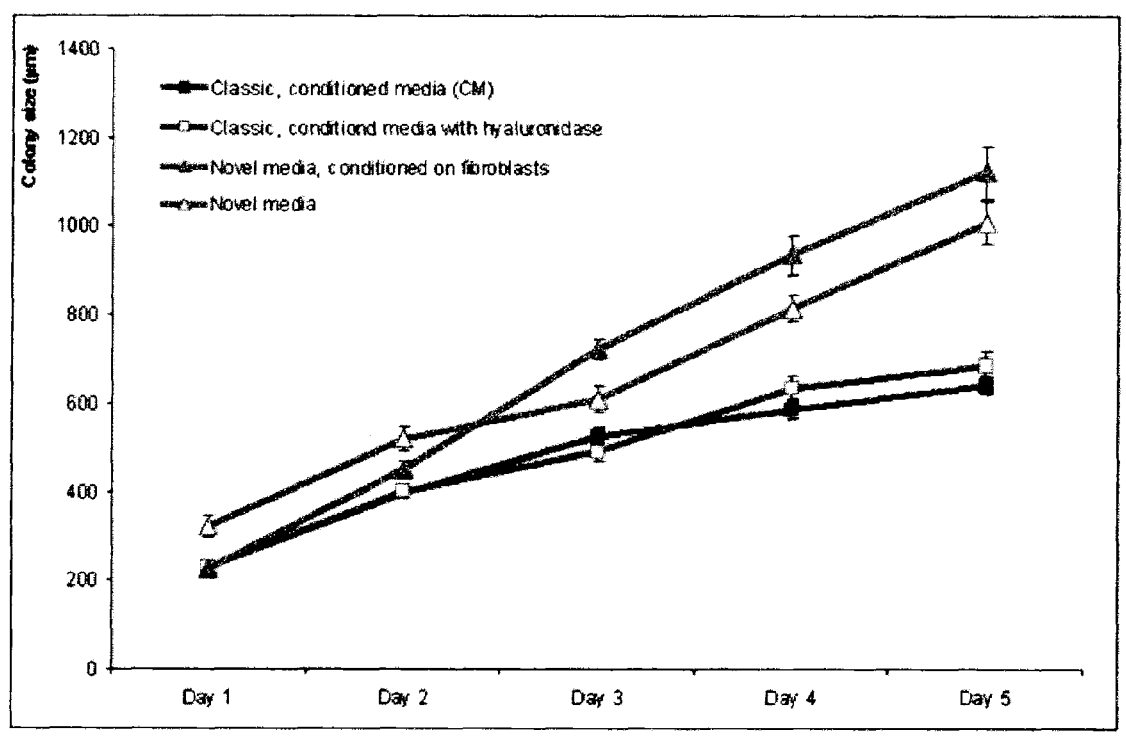
FIG. 1 is a graph representing cell growth curves in the presence of the indicated media.

The human embryonic stem cells growth in above media formulation was compared to a previously published formulation consisting of KO-DMEM, KO-Serum replacement L-Glutamine, NEAA. The media conditioning was performed on a mitomycin inactivated mouse embryonic fibroblast layer cultivated at a density of 12×10^6 cells per 225 cm2, overnight at 37° C. The colony sizes were measured daily and compared. The results are shown in FIG. 1.

The cells grown in the media formulation were further characterized. The stem cell colonies plated after the $3^{rd}$ passage in imaging chambers (Nunc) preserved the microscopic morphology with flat colonies, well delimited from the surrounding stroma. Labeling for stem cell markers Oct4 and TRA1-81 did show the persistence of the undifferentiated state after 3 passages. An in vitro spontaneous differentiation was studied using a serum containing media and labeling of the formed embryoid bodies demonstrated the presence of cells from all three germinal layers: ectoderm, mesoderm and endoderm.

Figure 2A:
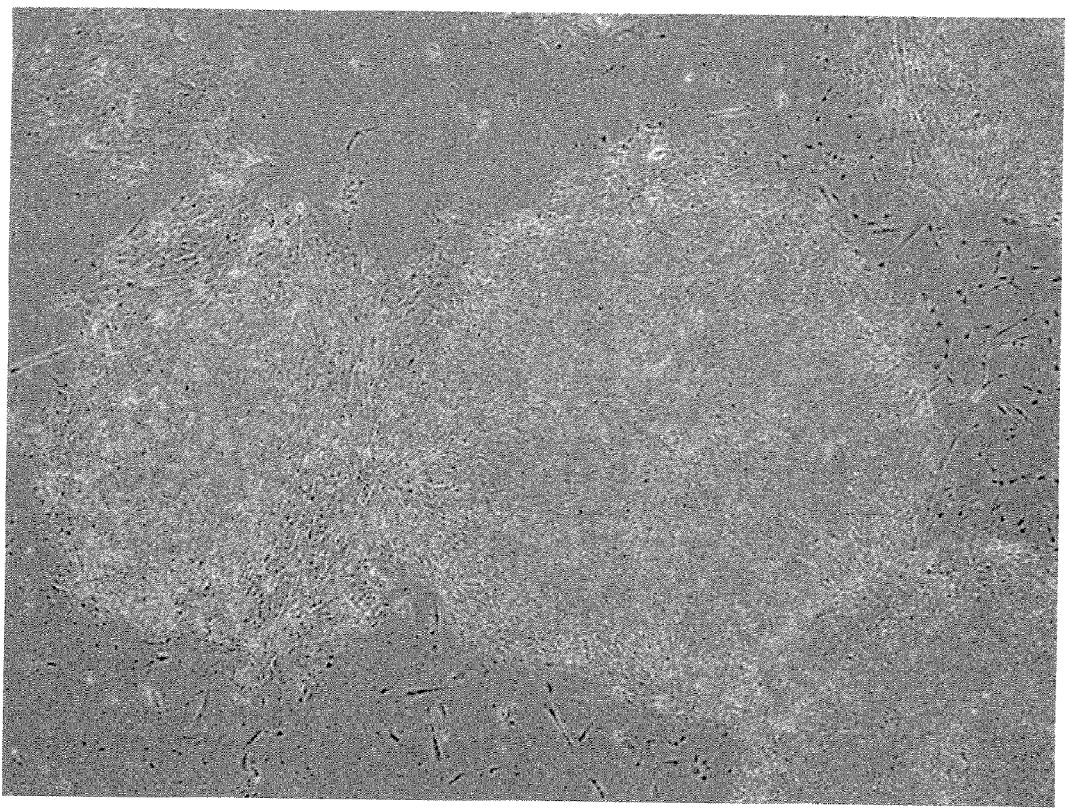
FIGS. 2A-2D illustrates stem cell colonies developed in the indicated media.
Figure 2B:
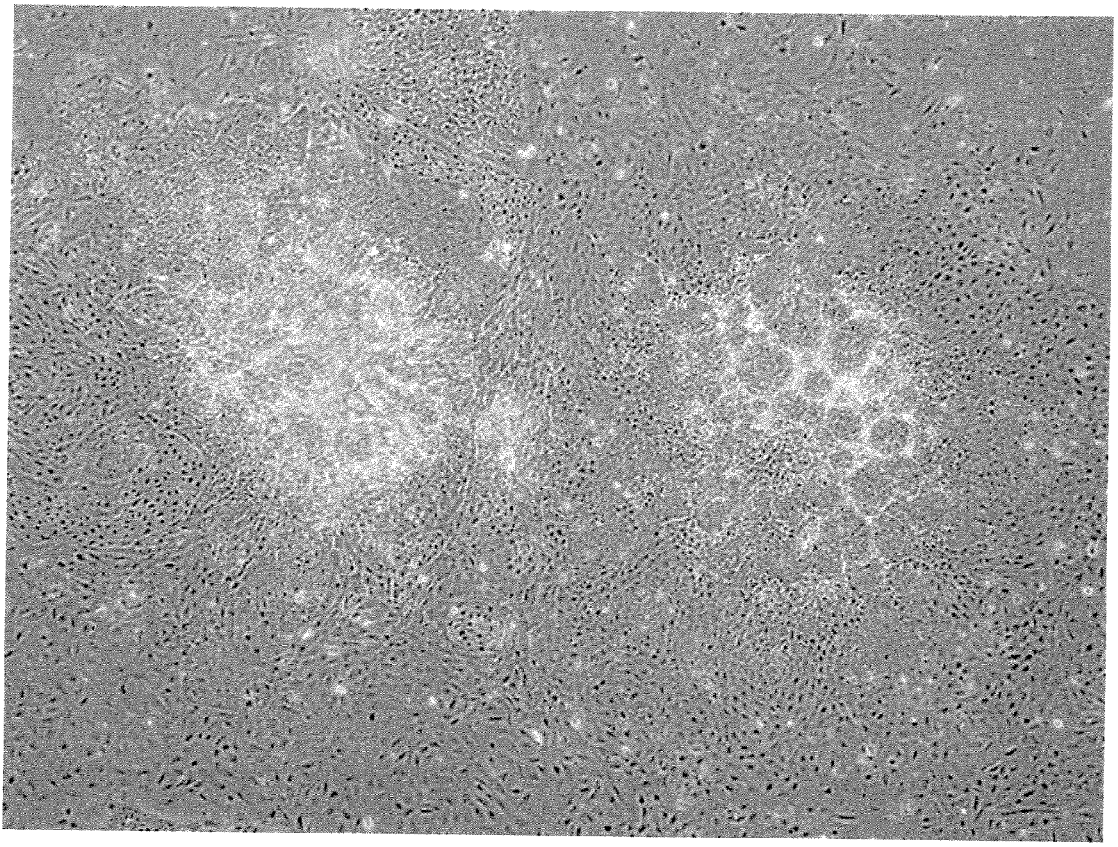
Figure 2C:
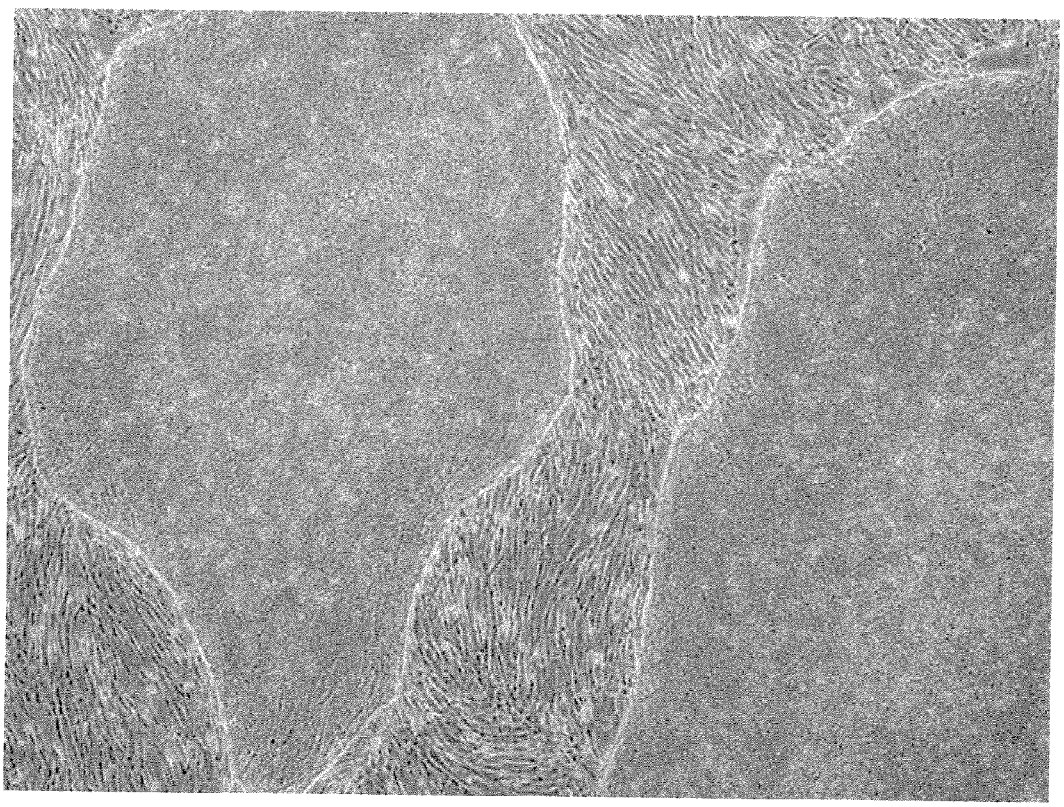
Figure 2D:
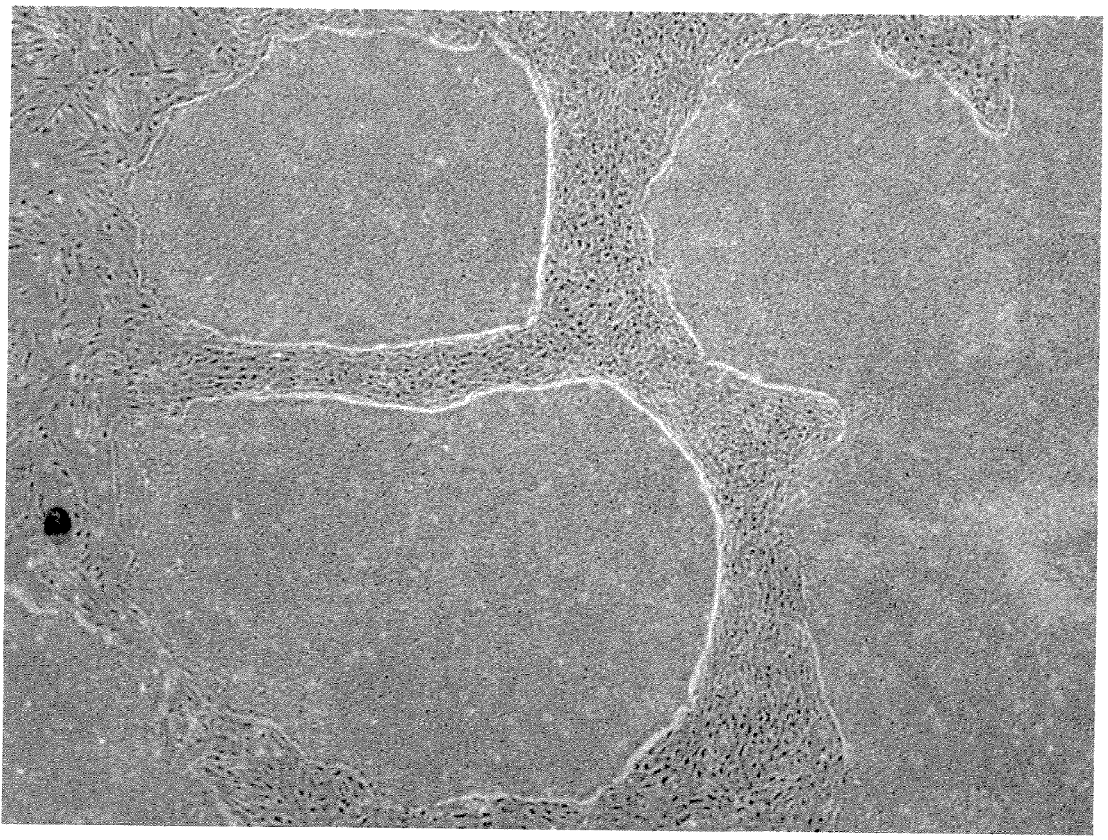

As illustrated in FIG. 2, stem cell colonies developed as expected in the classic media formulation (FIG. 2A). Without conditioning the media based on serum replacement caused massive differentiation (FIG. 2B). The serum free media formulation developed large homogenous colonies with smooth surfaces and abundant surrounding stroma (FIG. 2C). Without hyaluronidase the colonies had more fuzzy delimitation and tendency to differentiate (FIG. 2D).

Example 2

The example includes data in which media formulations were used to derive new stem cell lines.

Figure 3A:
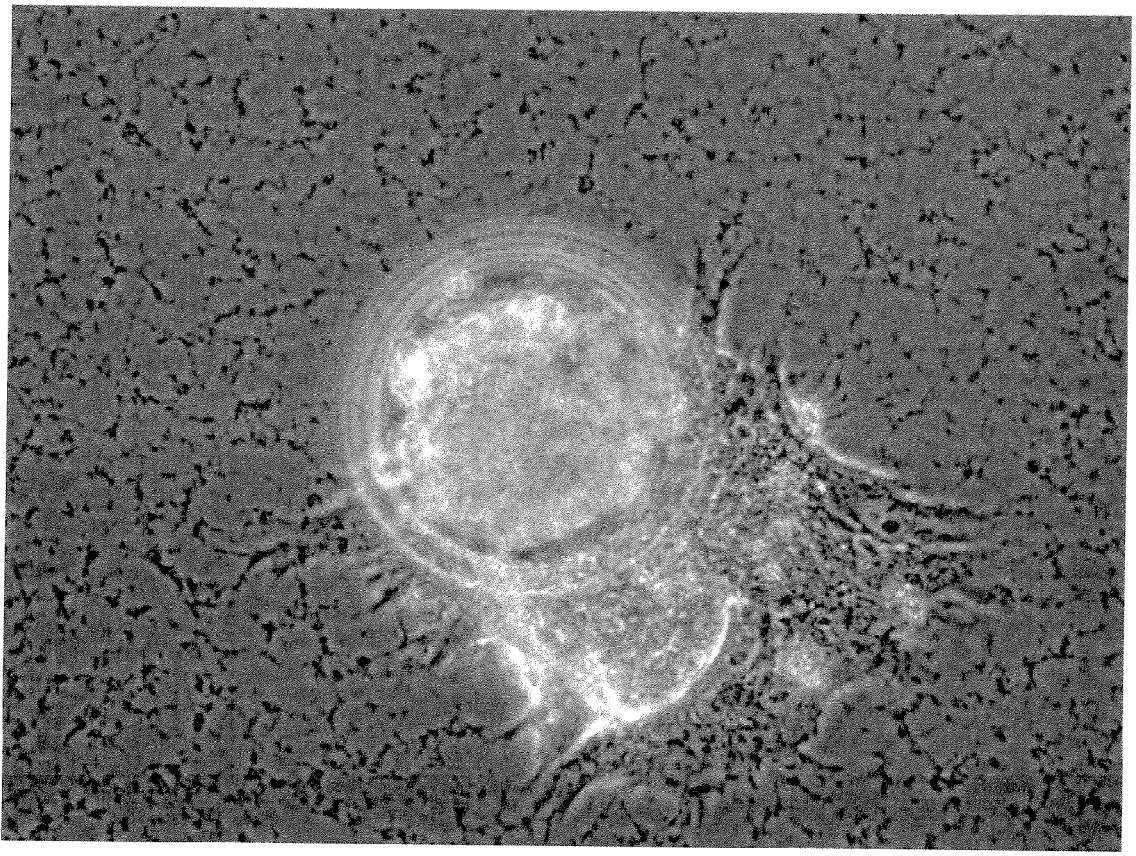
Figure 3B:
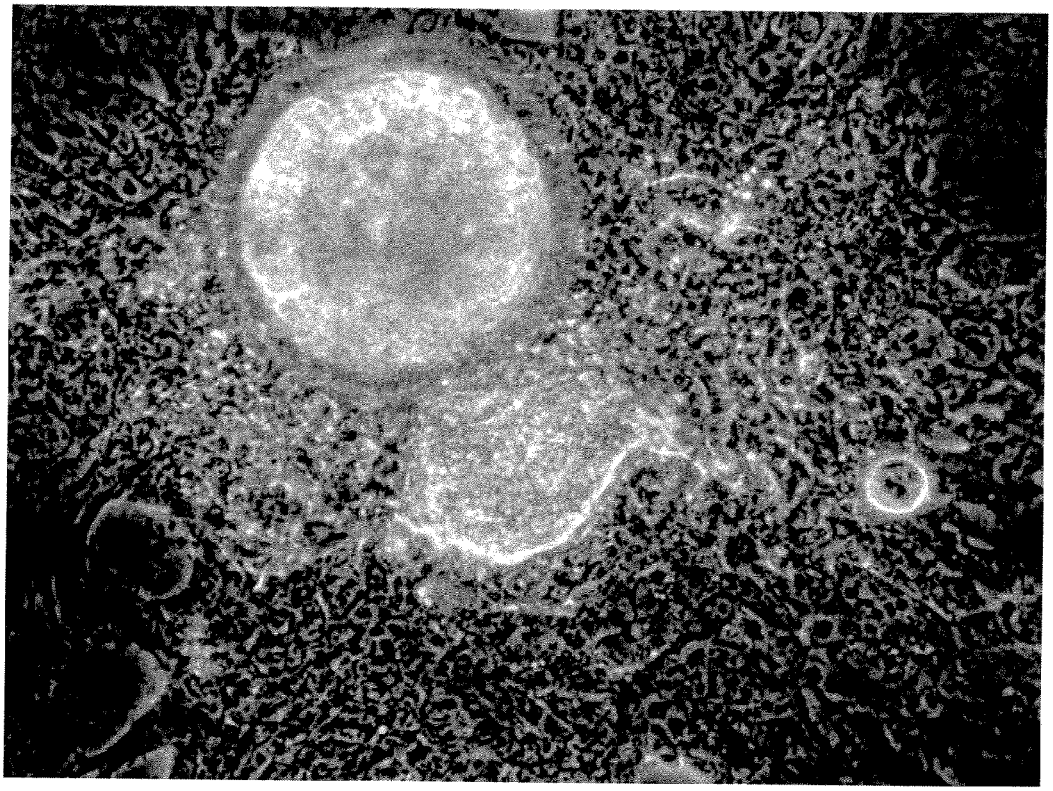
Figure 3C:
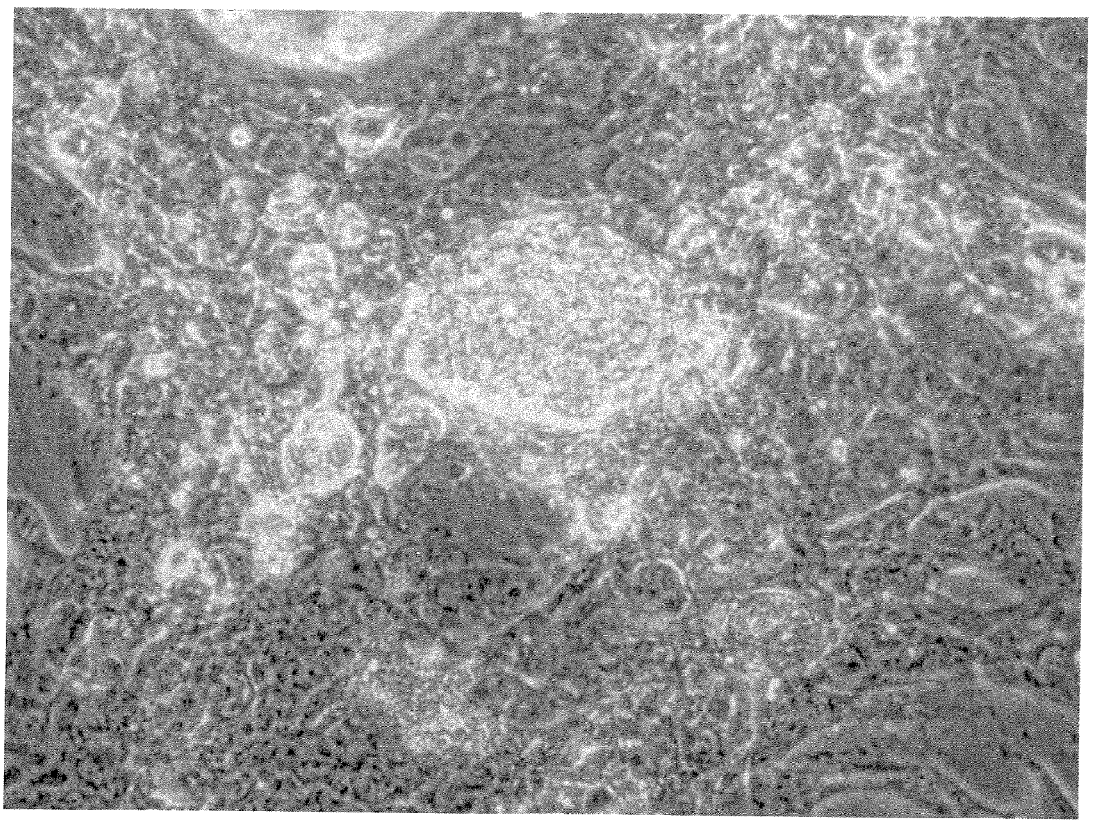

Frozen blastocysts were obtained by consented donation from the West Coast fertility Clinic. After thawing and maturation in M2 media (Irvine Scientific), the blastocysts were assisted hatched or spontaneously hatched in the exemplary Media Formulation in Example 1. The hatched blastocysts were than transferred to polystyrene wells coated with Matrigel 1:30. After an initial expansion, when the inner cell mass growth was limited by the invading trophoblastic cells, the inner cell mass (ICM) was mechanically extracted using fine needles and separately plated on Matrigel in the novel media formulation. After another 7 days the colonies started to grow with typical morphology (FIG. 3)—small, round, compact immobile cells with a nucleus to cytoplasm proportion of about 80 to 95%, one or multiple prominent nucleoli are visible, and the colonies are sharply delimited from surrounding cells which can be fibroblasts, trophoblasts or spontaneously differentiated cells that for stroma. The new stem cells were characterized using previously described methods (Hoffman and Carpenter, *Nature Biotechnol.* 23:699 (2005); Richards et al., *Nature Biotechnol.* 20:933 (2002); and Xu et al., *Nature Biotechnol.* 19:971 (2001)). This study demonstrates the efficacy of the proposed media composition in deriving new stem cell lines without inactivated feeder cells.

Example 3

This example describes media formulations used to expand human embryonic stem cells (hESC) for multiple passages and maintenance of pluripotency and normal karyotype. Identical stem cell flasks were plated with similar densities and fed with either a) a previously described conditioned media (CM), or b) exemplary invention media formulation described below:

| Component | Vendor | Cat # | Vol used | Stock Conc. | Final Conc. |
|---|---|---|---|---|---|
| DMEM/F-12 low osmolality | Gibco | 12660-012 | 467.5 ml | 1x | 1x |
| Non essential amino acids | Gibco | 11140 | 5 ml | 100x | 1x |
| Glutamax | Gibco | 35050 | 5 ml | 100x | 1x |
| Pyruvate | Gibco | 11360 | 2.5 ml | 100x | 0.5x |
| Human Albumin | Sigma | A1887 | 12.5 ml | 20% | 0.5% |
| Ethanolamine | Sigma | 411000 | 5 µl | 2 mg/ml | 20 µg/ml |
| Insulin | Sigma | I8405 | 500 µl | 5 mg/ml | 5 µg/ml |
| Transferrin | Sigma | T0665 | 250 µl | 20 mg/ml | 10 µg/ml |
| Selenite | Sigma | S9133 | 50 µl | 10 ug/ml | 1 ng/ml |
| T3 | Sigma | T0397 | 50 µl | 0.4 mg/ml | 4 ng/ml |
| Beta mercapto ethanol | Sigma | M7522 | 35 µl | 1.43M | 100 µM |

The exemplary invention media formulation was supplemented at feeding time with 10 ng/ml or 20 ng/ml basic FGF and 0 or 1 µg/ml Hyaluronidase. The CM media was formulated as previously described: KO-DMEM, 20% KO-Serum replacement, Non essential amino acids 1×, L-Glutamine 2 mM, β-mercaptoethanol 100 µM, bFGF 5 ng/ml. This composition is incubated overnight on a confluent and mitotically inactivated mouse embryonic fibroblast culture and 10 ng/ml bFGF is added prior to use for the culture of human embryonic stem cells.

The cultures were fed daily and passaged weekly at 1:3 or 1:4 ratios in 75 cm2 plastic flasks coated overnight with 1:30 diluted growth factor reduced Matrigel. The cultures were maintained at 37° C. and in 5% CO2 atmosphere. The passage was performed by enzymatic dissociation using collagenase IV (approximately 1 mg/ml) for 5-7 minutes followed by rinsing with Ca and Mg free phosphate buffer, mechanical dissociation with a cell scraper in media, than the partially dissociated cellular agglomerates were plated in the new flasks after 1:3 or 1:4 dilution.

In order to assess the potential to differentiate toward neural cells, after 5 passages in exemplary invention media formulation, the stem cells were dissociated and differentiated using retinoic acid towards neural lineages. A smaller culture sample was used to perform a karyotype analysis.

Figure 4:
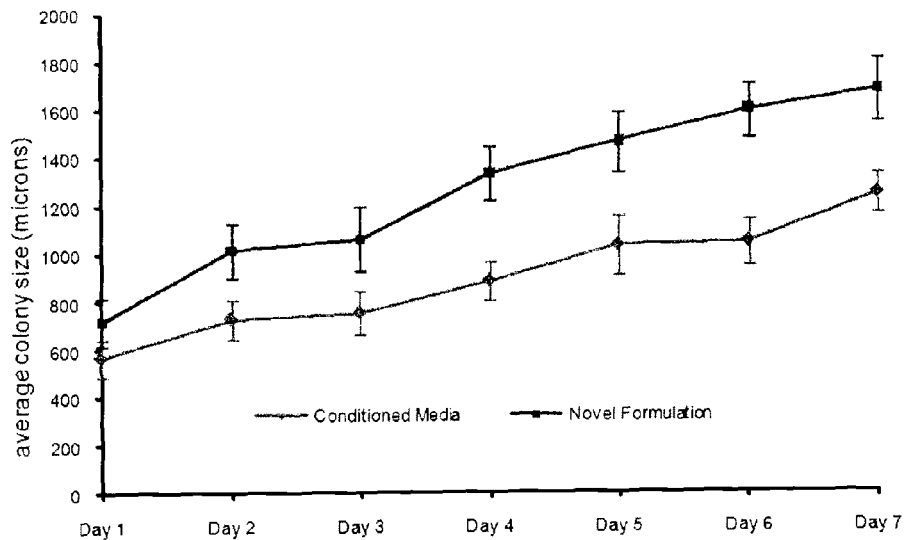
FIG. 4 illustrates growth of colonies over multiple days and passages in exemplary invention media formulation and conditioned media.
Figure 5:
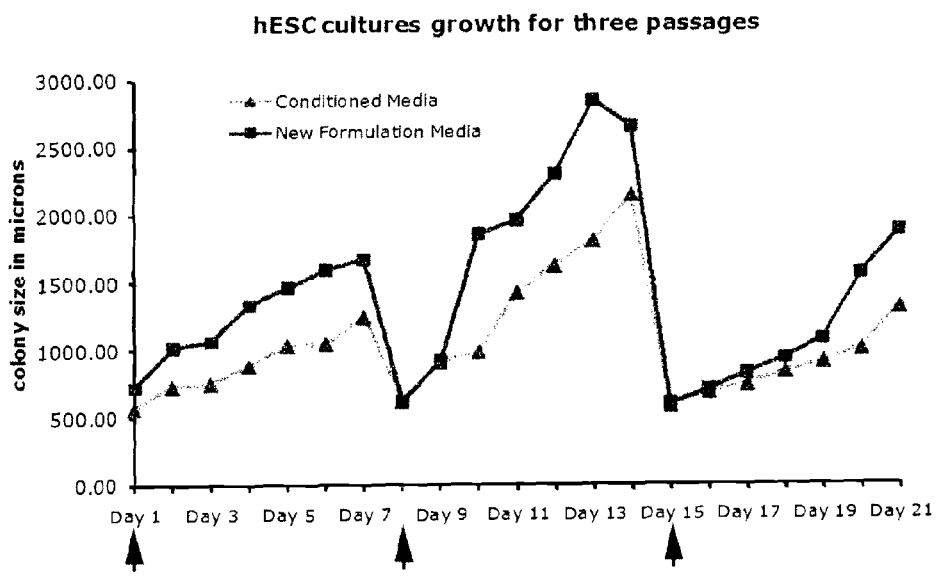
FIG. 5 illustrates sustained enhanced growth of hESCs in exemplary invention media containing 20 ng/ml bFGF and 1 µg/ml hyaluronidase over three passages (arrows indicate passage).

Each day, ten randomly selected colonies in each flask were subjected to measurement using an microscope ocular inserted micrometric reticule and each corresponding day measurement was averaged over multiple passages. In the exemplary invention media formulation stem cell colonies grew faster and larger (FIGS. 4 and 5).

Figure 6:
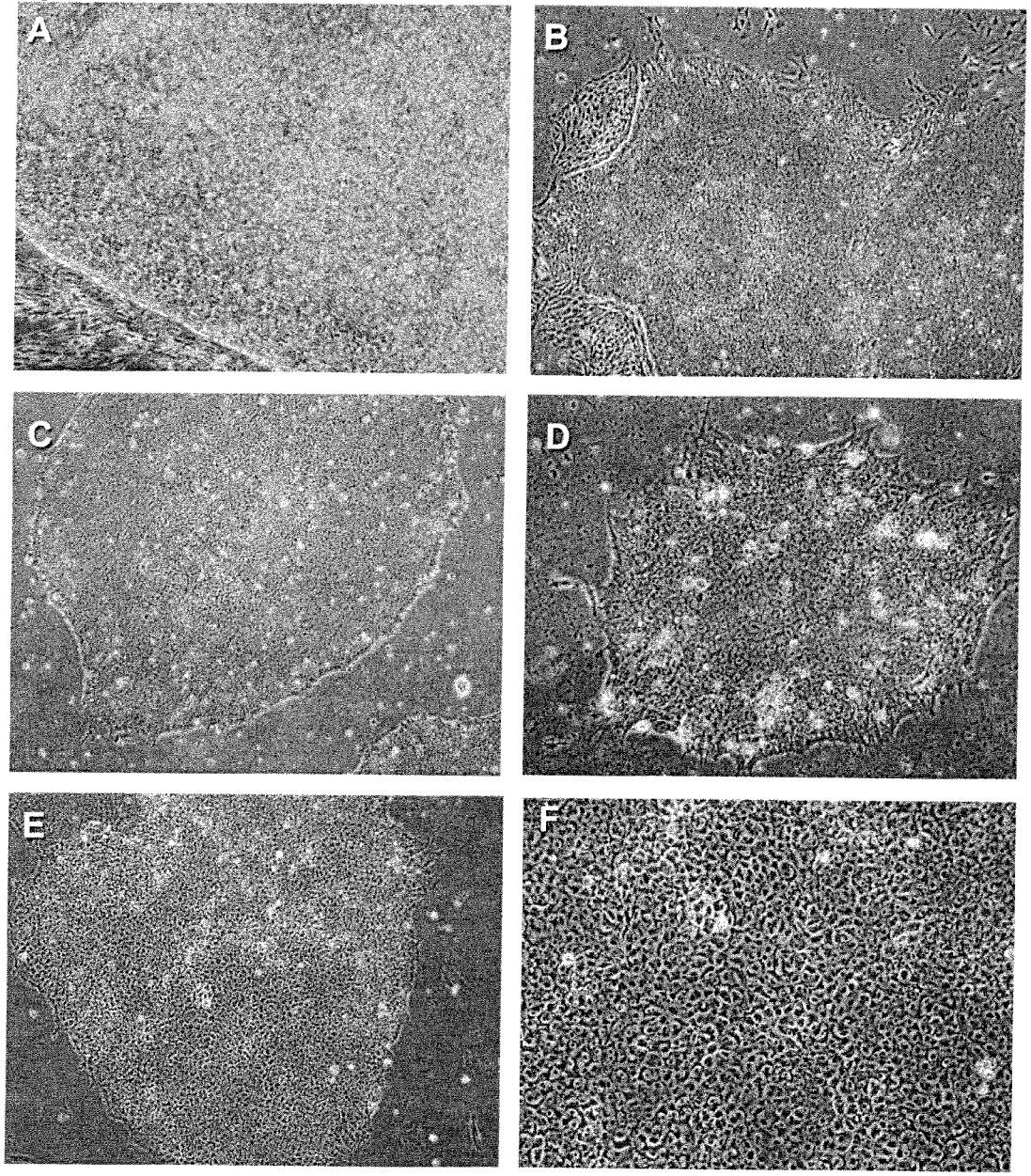

The spontaneously differentiating cells that arose from the hESC colonies grown in the exemplary invention media formulation, resulted in epithelial morphology, with some tendencies to rosette formations. The exemplary invention media formulation manifested a clear tendency towards ectodermal differentiation of the stem cells, while maintaining pluripotency (FIG. 6B). The formulation that did not cause a clear and immediate neural differentiation, but biased the culture towards the ectodermal lineage. When differentiated into neural cell types, the cultures expressed a high yield and purity of neural populations, compared to the cultures grown in conditioned media (CM). When the embryonic stem cells are grown in CM, and the differentiation is initiated in a typical differentiation media, there is an initial drop in the number of cells caused by cellular death, which reduces the efficiency of the differentiation. In the exemplary invention media formulation, at initiation of differentiation, the initial drop in cell counts was absent and resulted in significantly larger numbers of differentiated neural cells (FIG. 10).

The addition of hyaluronidase shifts the differentiation tendency toward the endodermal lineage, while the removal of hyaluronidase shifts the culture toward ectodermal lineage. Addition of hyaluronidase to the media corrected the tendency to ectodermal differentiation resulting in typical stem cell colonies, with minimal spontaneously differentiating cells (FIGS. 6C, D, E, F).

Prolonged exposure to hyaluronidase caused differentiation toward the endodermal lineage, characterized by large polygonal cells with abundant cytoplasm and prominent nuclei. These cells were alpha-feto protein positive, indicative of endodermal lineages.

Figure 7:
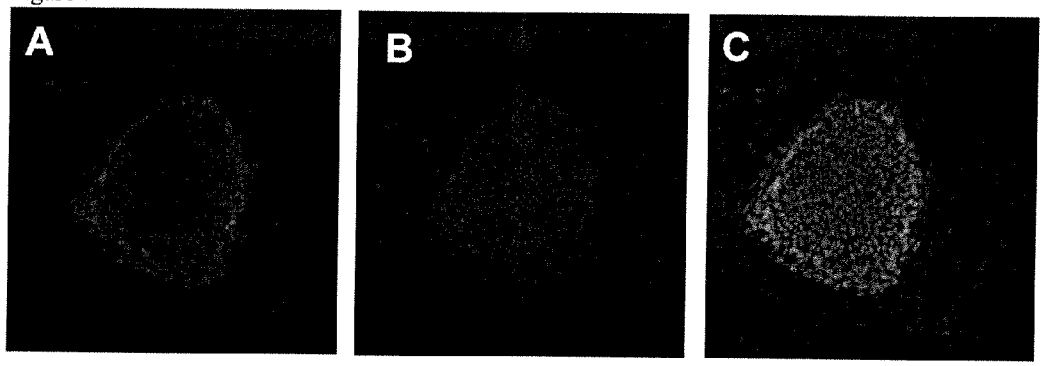

By feeding the stem cell cultures in exemplary invention media formulation with the increase of the bFGF concentration up to 20 ng/ml and addition of hyaluronidase at 1 µg/ml for two days in each passage cycle, undifferentiated pluripotent stem cell cultures were grown for many passages without signs of extensive differentiation (FIGS. 5 and 6C, D, E, F). Stem cell cultures grown in the exemplary invention media formulation maintained pluripotency over more than 5 passages, evidenced by expression of the pluripotency markers Oct4 and SSEA4 (FIG. 7).

Figure 8:
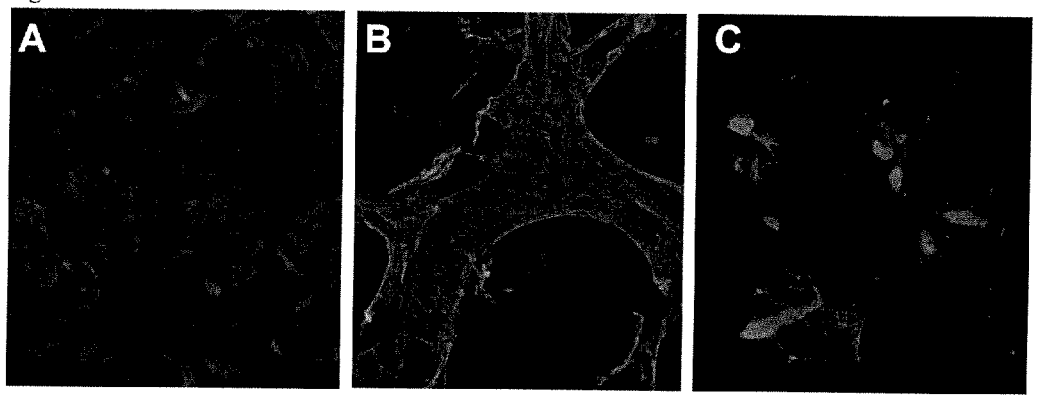

In vitro differentiation of human embryonic stem cells grown in the exemplary invention media formulation supplemented with hyaluronidase resulted in populations belonging to all germ layers (ectoderm, mesoderm and endoderm, FIG. 8).

Karyotype analysis was performed by an independent third party service provider (Genzyme Genetics, Orange, Calif.) and was found to be normal (46, XX) after 7 passages of growth in the novel media formulation.

After extensive growth of hESCs in the exemplary invention media formulation the typical stem cell phenotype was maintained, evidenced by typical colony morphology, expression of the stemness markers Oct4 and SSEA4, and pluripotency (ectoderm, mesoderm, endoderm). After 5 passages the cultures manifested a tendency to differentiate preferentially towards ectodermal lineages in exemplary invention media, if unsupplemented with hyaluronidase.

The yield of neural cells was higher in the stem cell cultures in exemplary invention media without the addition of hyaluronidase compared to cells grown in the CM formulation. This outcome is beneficial when ectodermal lineage specificity is desired (for example neuro-ectoderm) (FIGS. 9 and 10).

The ectodermal differentiation tendencies can be corrected using hyaluronidase for 1-2 days per passage cycle and the increasing FGF concentration to 20 µg/ml.

Extensive use of hyaluronidase in low concentration results in a tendency of endodermal differentiation of the stem cell cultures. This outcome is beneficial when endodermal lineage specificity is desired (for example hepatocytes) (FIGS. 9 and 10).

This hereby incorporates by reference the ASCII text file (73 kb), entitled, Sequence Listing, created Jul. 26, 2011.

The invention claimed is:

1. A method of biasing human embryonic stem cells (hESCs) towards endodermal lineage without substantial differentiation the method comprising:
culturing hESCs that were never previously exposed to a supplement of hyaluronidase, wherein the never previously exposed hESCs are cultured in exemplary invention media formulation
supplemented with a hyaluronidase concentration that permits biasing towards endodermal lineage, to generate hESCs biased towards endodermal lineage in one of a plurality of increasing concentrations of hyaluronidase, starting from about 0 ug/ml of hyaluronidase and increasing to a concentration of hyaluronidase effective to bias towards endodermal lineage, added to a media formulation that is exemplary invention media formulation, whereby increasing the concentration of hyaluronidase above about 0 ug/ml selectively biases the differential tendency of the hESCs towards endodermal lineage,
wherein said exemplary invention media formulation has 1×DMEM/F-12 low osmolality (467.5 mL); 5 mL of 1× nonessential amino acids, 5 mL of 1× Glutamax (L-alanylglutamine), 2.5 mL of 0.5× pyruvate, 0.5% human albumin, 20 ug/mL ethanolamine, 5 ug/mL insulin, 10 ug/mL transferrin, 1 ng/mL selenite, 4 ng/mL T3 (thyroid hormone), and 100 uM beta-mercaptoethanol, 494 mL final volume.

2. The method of biasing of claim 1, said exemplary invention media formulation further comprising one or more essential amino acids, wherein the essential amino acids comprise arginine; cystine; histidine; isoleucine; leucine; methionine; phenylalanine; threonine; tryptophan; tyrosine; and valine.

3. The method of biasing of claim 1, said exemplary invention media formulation further comprising an extracellular matrix of laminin or fibronectin.

4. The method of biasing of claim 3 the method further comprising culturing each of said hESCs in the exemplary invention media formulation on the extracellular matrix for a period of time allowing the hESCs to increase in number by 25%, 50%, 75%, 100% or more.

5. The method of biasing of claim 3 the method further comprising culturing each of said hESCs in the exemplary invention media formulation on the extracellular matrix for at least 30 minutes to 48 hours.

6. The method of biasing of claim 1 wherein the concentration of hyaluronidase that biases towards endodermal lineage is between about 1 to about 10 µg/ml.

7. The method of biasing of claim 1 wherein the concentration of hyaluronidase that biases towards endodermal lineage is between about 1 to about 25 µg/ml.

8. The method of biasing of claim 1 wherein the concentration of hyaluronidase that biases towards endodermal lineage is between about 1 to about 50 µg/ml.

9. The method of biasing of claim 1 wherein the concentration of hyaluronidase that biases towards endodermal lineage is between about 1 to about 100 µg/ml.

10. The method of claim 1, each of said exemplary invention media formulation further comprising fibroblast growth factor (FGF).

\* \* \* \* \*

SEQUENCE LISTING

```
<160> NUMBER OF SEQ ID NOS: 32

<210> SEQ ID NO 1
<211> LENGTH: 435
<212> TYPE: PRT
<213> ORGANISM: Homo sapiens

<400> SEQUENCE: 1

Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255
```

```
Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435

<210> SEQ ID NO 2
<211> LENGTH: 450
<212> TYPE: PRT
<213> ORGANISM: Bos taurus

<400> SEQUENCE: 2

Met Arg Pro Phe Ser Leu Glu Val Ser Leu His Leu Pro Trp Ala Met
1               5                   10                  15

Ala Ala His Leu Leu Pro Val Cys Thr Leu Phe Leu Asn Leu Leu Ser
            20                  25                  30

Met Thr Gln Gly Ser Arg Asp Pro Val Val Pro Asn Gln Pro Phe Thr
        35                  40                  45

Thr Ile Trp Asn Ala Asn Thr Glu Trp Cys Met Lys Lys His Gly Val
    50                  55                  60

Asp Val Asp Ile Ser Ile Phe Asp Val Val Thr Asn Pro Gly Gln Thr
65                  70                  75                  80

Phe Arg Gly Pro Asn Met Thr Ile Phe Tyr Ser Ser Gln Leu Gly Thr
                85                  90                  95

Tyr Pro Tyr Tyr Thr Ser Ala Gly Glu Pro Val Phe Gly Gly Leu Pro
            100                 105                 110

Gln Asn Ala Ser Leu Asn Ala His Leu Ala Arg Thr Phe Gln Asp Ile
        115                 120                 125

Leu Ala Ala Met Pro Glu Pro Arg Phe Ser Gly Leu Ala Val Ile Asp
    130                 135                 140

Trp Glu Ala Trp Arg Pro Arg Trp Ala Phe Asn Trp Asp Thr Lys Asp
145                 150                 155                 160

Ile Tyr Arg Gln Arg Ser Arg Ala Leu Val Gln Lys Gln His Pro Asp
                165                 170                 175

Trp Leu Ala Pro Arg Val Glu Ala Ala Gln Asp Gln Phe Glu Gly
            180                 185                 190
```

```
Ala Ala Glu Glu Trp Met Ala Gly Thr Leu Lys Leu Gly Gln Ala Leu
            195                 200                 205

Arg Pro Gln Gly Leu Trp Gly Phe Tyr Asn Phe Pro Glu Cys Tyr Asn
        210                 215                 220

Tyr Asp Phe Lys Ser Pro Asn Tyr Thr Gly Arg Cys Pro Leu Asn Ile
225                 230                 235                 240

Cys Ala Gln Asn Asp Gln Leu Gly Trp Leu Trp Gly Gln Ser Arg Ala
            245                 250                 255

Leu Tyr Pro Ser Ile Tyr Leu Pro Ala Ala Leu Glu Gly Thr Lys Lys
        260                 265                 270

Thr Gln Met Phe Val Gln His Arg Val Ala Glu Ala Phe Arg Val Ala
    275                 280                 285

Ala Gly Ala Gly Asp Pro Lys Leu Pro Val Leu Pro Tyr Met Gln Leu
        290                 295                 300

Phe Tyr Asp Met Thr Asn His Phe Leu Pro Ala Glu Glu Leu Glu His
305                 310                 315                 320

Ser Leu Gly Glu Ser Ala Ala Gln Gly Ala Gly Val Val Leu Trp
            325                 330                 335

Val Ser Trp Leu Ser Thr Ser Thr Lys Glu Ser Cys Gln Ala Ile Lys
        340                 345                 350

Glu Tyr Val Asp Thr Thr Leu Gly Pro Ser Ile Leu Asn Val Thr Ser
    355                 360                 365

Gly Ala Arg Leu Cys Ser Gln Val Leu Cys Ser Gly His Gly Arg Cys
        370                 375                 380

Ala Arg Arg Pro Ser Tyr Pro Lys Ala Arg Leu Ile Leu Asn Ser Thr
385                 390                 395                 400

Ser Phe Ser Ile Lys Pro Thr Pro Gly Gly Pro Leu Thr Leu Gln
            405                 410                 415

Gly Ala Leu Ser Leu Glu Asp Arg Leu Arg Met Ala Val Glu Phe Glu
        420                 425                 430

Cys Arg Cys Tyr Arg Gly Trp Arg Gly Thr Arg Cys Glu Gln Trp Gly
    435                 440                 445

Met Trp
    450

<210> SEQ ID NO 3
<211> LENGTH: 462
<212> TYPE: PRT
<213> ORGANISM: Mus musculus

<400> SEQUENCE: 3

Met Leu Gly Leu Thr Gln His Ala Gln Lys Val Trp Arg Met Lys Pro
1               5                   10                  15

Phe Ser Pro Glu Val Ser Pro Gly Ser Ser Pro Ala Thr Ala Gly His
            20                  25                  30

Leu Leu Arg Ile Ser Thr Leu Phe Leu Thr Leu Glu Leu Ala Gln
        35                  40                  45

Val Cys Arg Gly Ser Val Val Ser Asn Arg Pro Phe Ile Thr Val Trp
    50                  55                  60

Asn Gly Asp Thr His Trp Cys Leu Thr Glu Tyr Gly Val Asp Val Asp
65                  70                  75                  80

Val Ser Val Phe Asp Val Val Ala Asn Lys Glu Gln Ser Phe Gln Gly
            85                  90                  95

Ser Asn Met Thr Ile Phe Tyr Arg Glu Glu Leu Gly Tyr Pro Tyr
            100                 105                 110
```

```
Tyr Thr Pro Thr Gly Glu Pro Val Phe Gly Gly Leu Pro Gln Asn Ala
            115                 120                 125

Ser Leu Val Thr His Leu Ala His Thr Phe Gln Asp Ile Lys Ala Ala
130                 135                 140

Met Pro Glu Pro Asp Phe Ser Gly Leu Ala Val Ile Asp Trp Glu Ala
145                 150                 155                 160

Trp Arg Pro Arg Trp Ala Phe Asn Trp Asp Ser Lys Asp Ile Tyr Arg
                165                 170                 175

Gln Arg Ser Met Glu Leu Val Gln Ala Glu His Pro Asp Trp Pro Glu
            180                 185                 190

Thr Leu Val Glu Ala Ala Lys Asn Gln Phe Gln Glu Ala Ala Glu
        195                 200                 205

Ala Trp Met Ala Gly Thr Leu Gln Leu Gly Gln Val Leu Arg Pro Arg
210                 215                 220

Gly Leu Trp Gly Tyr Tyr Gly Phe Pro Asp Cys Tyr Asn Asn Asp Phe
225                 230                 235                 240

Leu Ser Leu Asn Tyr Thr Gly Gln Cys Pro Val Phe Val Arg Asp Gln
                245                 250                 255

Asn Asp Gln Leu Gly Trp Leu Trp Asn Gln Ser Tyr Ala Leu Tyr Pro
            260                 265                 270

Ser Ile Tyr Leu Pro Ala Ala Leu Met Gly Thr Gly Lys Ser Gln Met
        275                 280                 285

Tyr Val Arg His Arg Val Gln Glu Ala Leu Arg Val Ala Ile Val Ser
290                 295                 300

Arg Asp Pro His Val Pro Val Met Pro Tyr Val Gln Ile Phe Tyr Glu
305                 310                 315                 320

Met Thr Asp Tyr Leu Leu Pro Leu Glu Glu Leu Glu His Ser Leu Gly
                325                 330                 335

Glu Ser Ala Ala Gln Gly Val Ala Gly Ala Val Leu Trp Leu Ser Ser
            340                 345                 350

Asp Lys Thr Ser Thr Lys Glu Ser Cys Gln Ala Ile Lys Ala Tyr Met
        355                 360                 365

Asp Ser Thr Leu Gly Pro Phe Ile Val Asn Val Thr Ser Ala Ala Leu
370                 375                 380

Leu Cys Ser Glu Ala Leu Cys Ser Gly His Gly Arg Cys Val Arg His
385                 390                 395                 400

Pro Ser Tyr Pro Glu Ala Leu Leu Thr Leu Asn Pro Ala Ser Phe Ser
                405                 410                 415

Ile Glu Leu Thr His Asp Gly Arg Pro Ser Leu Lys Gly Thr Leu
            420                 425                 430

Ser Leu Lys Asp Arg Ala Gln Met Ala Met Lys Phe Arg Cys Arg Cys
        435                 440                 445

Tyr Arg Gly Trp Arg Gly Lys Trp Cys Asp Lys Arg Gly Met
450                 455                 460

<210> SEQ ID NO 4
<211> LENGTH: 473
<212> TYPE: PRT
<213> ORGANISM: Homo sapiens

<400> SEQUENCE: 4

Met Arg Ala Gly Pro Gly Pro Thr Val Thr Leu Ala Leu Val Leu Ala
1               5                   10                  15

Val Ala Trp Ala Met Glu Leu Lys Pro Thr Ala Pro Pro Ile Phe Thr
            20                  25                  30
```

```
Gly Arg Pro Phe Val Val Ala Trp Asp Val Pro Thr Gln Asp Cys Gly
            35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
                100                 105                 110

Leu Gln Lys Arg Val Glu His Tyr Ile Arg Thr Gln Glu Ser Ala Gly
            115                 120                 125

Leu Ala Val Ile Asp Trp Glu Asp Trp Arg Pro Val Trp Val Arg Asn
            130                 135                 140

Trp Gln Asp Lys Asp Val Tyr Arg Arg Leu Ser Arg Gln Leu Val Ala
145                 150                 155                 160

Ser Arg His Pro Asp Trp Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
            195                 200                 205

Pro Asp Cys Tyr Asn His Asp Tyr Val Gln Asn Trp Glu Ser Tyr Thr
            210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
                260                 265                 270

Gln Glu Ala Leu Arg Val Ala Arg Thr His His Ala Asn His Ala Leu
            275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
            355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
                420                 425                 430

Trp Ser Gly Glu Gln Cys Gln Trp Asp His Arg Gln Ala Ala Gly Gly
            435                 440                 445

Ala Ser Glu Ala Trp Ala Gly Ser His Leu Thr Ser Leu Leu Ala Leu
    450                 455                 460
```

```
Ala Ala Leu Ala Phe Thr Trp Thr Leu
465                 470

<210> SEQ ID NO 5
<211> LENGTH: 473
<212> TYPE: PRT
<213> ORGANISM: Mus musculus

<400> SEQUENCE: 5

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Ile Phe Thr
            20                  25                  30

Gly Arg Pro Phe Val Val Ala Trp Asn Val Pro Thr Gln Glu Cys Ala
            35                  40                  45

Pro Arg His Lys Val Pro Leu Asp Leu Arg Ala Phe Asp Val Lys Ala
        50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Glu Ser Tyr Thr
210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Val His Ser Arg Asn Phe Val Ser Phe Arg Val
            260                 265                 270

Arg Glu Ala Leu Arg Val Ala His Thr His Ala Asn His Ala Leu
        275                 280                 285

Pro Val Tyr Val Phe Thr Arg Pro Thr Tyr Thr Arg Gly Leu Thr Gly
290                 295                 300

Leu Ser Gln Val Asp Leu Ile Ser Thr Ile Gly Glu Ser Ala Ala Leu
305                 310                 315                 320

Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
            340                 345                 350

Pro Tyr Ile Val Asn Val Ser Trp Ala Thr Gln Tyr Cys Ser Trp Thr
        355                 360                 365
```

-continued

Gln Cys His Gly His Gly Arg Cys Val Arg Asn Pro Ser Ala Asn
        370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445

Ala Ser Arg Ala Trp Ala Gly Ser His Leu Thr Ser Leu Leu Gly Leu
    450                 455                 460

Val Ala Val Ala Leu Thr Trp Thr Leu
465                 470

<210> SEQ ID NO 6
<211> LENGTH: 417
<212> TYPE: PRT
<213> ORGANISM: Homo sapiens

<400> SEQUENCE: 6

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
            275                 280                 285

His Arg Arg Ser Gly Arg Phe Leu Ser Gln Asp Asp Leu Val Gln Ser
        290                 295                 300

Ile Gly Val Ser Ala Ala Leu Gly Ala Ala Gly Val Val Leu Trp Gly
305                 310                 315                 320

Asp Leu Ser Leu Ser Ser Ser Glu Glu Glu Cys Trp His Leu His Asp
                325                 330                 335

Tyr Leu Val Asp Thr Leu Gly Pro Tyr Val Ile Asn Val Thr Arg Ala
                340                 345                 350

Ala Met Ala Cys Ser His Gln Arg Cys His Gly His Gly Arg Cys Ala
            355                 360                 365

Arg Arg Asp Pro Gly Gln Met Glu Ala Phe Leu His Leu Trp Pro Asp
370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val

<210> SEQ ID NO 7
<211> LENGTH: 481
<212> TYPE: PRT
<213> ORGANISM: Homo sapiens

<400> SEQUENCE: 7

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Tyr Leu Tyr Pro Asp Cys His
210                 215                 220

```
Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
            245                 250                 255

Ala Leu Tyr Pro Ser Ile Cys Val Trp Lys Ser Leu Gly Asp Ser Glu
        260                 265                 270

Asn Ile Leu Arg Phe Ser Lys Phe Arg Val His Glu Ser Met Arg Ile
    275                 280                 285

Ser Thr Met Thr Ser His Asp Tyr Ala Leu Pro Val Phe Val Tyr Thr
290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
            325                 330                 335

Val Ile Trp Gly Asp Met Asn Leu Thr Ala Ser Lys Ala Asn Cys Thr
        340                 345                 350

Lys Val Lys Gln Phe Val Ser Ser Asp Leu Gly Ser Tyr Ile Ala Asn
    355                 360                 365

Val Thr Arg Ala Ala Glu Val Cys Ser Leu His Leu Cys Arg Asn Asn
370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
            405                 410                 415

Val Lys Gly Lys Ala Ser Asp Thr Asp Leu Ala Val Met Ala Asp Thr
        420                 425                 430

Phe Ser Cys His Cys Tyr Gln Gly Tyr Glu Gly Ala Asp Cys Arg Glu
    435                 440                 445

Ile Lys Thr Ala Asp Gly Cys Ser Gly Val Ser Pro Ser Pro Gly Ser
450                 455                 460

Leu Met Thr Leu Cys Leu Leu Leu Ala Ser Tyr Arg Ser Ile Gln
465                 470                 475                 480

Leu

<210> SEQ ID NO 8
<211> LENGTH: 155
<212> TYPE: PRT
<213> ORGANISM: Homo sapiens

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
```

```
                  115                 120                 125
Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Mus musculus

<400> SEQUENCE: 9

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 10
<211> LENGTH: 155
<212> TYPE: PRT
<213> ORGANISM: Homo sapiens

<400> SEQUENCE: 10

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140
```

-continued

Ala Ile Leu Phe Leu Pro Met Ser Ala Lys Ser
145                 150                 155

<210> SEQ ID NO 11
<211> LENGTH: 154
<212> TYPE: PRT
<213> ORGANISM: Mus musculus

<400> SEQUENCE: 11

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 12
<211> LENGTH: 238
<212> TYPE: PRT
<213> ORGANISM: Homo sapiens

<400> SEQUENCE: 12

Met Gly Leu Ile Trp Leu Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
            20                  25                  30

Gly Gly Val Tyr Glu His Leu Gly Gly Ala Pro Arg Arg Arg Lys Leu
        35                  40                  45

Tyr Cys Ala Thr Lys Tyr His Leu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
            100                 105                 110

Ala Glu Cys Glu Phe Val Glu Arg Ile His Glu Leu Gly Tyr Asn Thr
        115                 120                 125

Tyr Ala Ser Arg Leu Tyr Arg Thr Val Ser Ser Thr Pro Gly Ala Arg
    130                 135                 140

Arg Gln Pro Ser Ala Glu Arg Leu Trp Tyr Val Ser Val Asn Gly Lys
145                 150                 155                 160

-continued

Gly Arg Pro Arg Arg Gly Phe Lys Thr Arg Thr Gln Lys Ser Ser
                165                 170                 175

Leu Phe Leu Pro Arg Val Leu Asp His Arg Asp His Glu Met Val Arg
            180                 185                 190

Gln Leu Gln Ser Gly Leu Pro Arg Pro Pro Gly Lys Gly Val Gln Pro
        195                 200                 205

Arg Arg Arg Arg Gln Lys Gln Ser Pro Asp Asn Leu Glu Pro Ser His
    210                 215                 220

Val Ala Ser Arg Leu Gly Ser Gln Leu Glu Ala Ser Ala His
225                 230                 235

<210> SEQ ID NO 13
<211> LENGTH: 204
<212> TYPE: PRT
<213> ORGANISM: Homo sapiens

<400> SEQUENCE: 13

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Ser
            100                 105                 110

Leu Leu Glu Leu Ser Pro Val Glu Arg Gly Val Val Ser Ile Phe Gly
        115                 120                 125

Val Ala Ser Arg Phe Phe Val Ala Met Ser Ser Lys Gly Lys Leu Tyr
    130                 135                 140

Gly Ser Pro Phe Phe Thr Asp Glu Cys Thr Phe Lys Glu Ile Leu Leu
145                 150                 155                 160

Pro Asn Asn Tyr Asn Ala Tyr Glu Ser Tyr Lys Tyr Pro Gly Met Phe
                165                 170                 175

Ile Ala Leu Ser Lys Asn Gly Lys Thr Lys Lys Gly Asn Arg Val Ser
            180                 185                 190

Pro Thr Met Lys Val Thr His Phe Leu Pro Arg Leu
        195                 200

<210> SEQ ID NO 14
<211> LENGTH: 268
<212> TYPE: PRT
<213> ORGANISM: Homo sapiens

<400> SEQUENCE: 14

Met Ser Leu Ser Phe Leu Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ser Ala Ser Ser Ser Pro Ala

```
            50                  55                  60
Ala Ser Leu Gly Ser Gln Gly Ser Gly Leu Glu Gln Ser Ser Phe Gln
 65                  70                  75                  80

Trp Ser Pro Ser Gly Arg Arg Thr Gly Ser Leu Tyr Cys Arg Val Gly
                 85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
            260                 265

<210> SEQ ID NO 15
<211> LENGTH: 208
<212> TYPE: PRT
<213> ORGANISM: Homo sapiens

<400> SEQUENCE: 15

Met Ala Leu Gly Gln Lys Leu Phe Ile Thr Met Ser Arg Gly Ala Gly
  1               5                  10                  15

Arg Leu Gln Gly Thr Leu Trp Ala Leu Val Phe Leu Gly Ile Leu Val
             20                  25                  30

Gly Met Val Val Pro Ser Pro Ala Gly Thr Arg Ala Asn Asn Thr Leu
         35                  40                  45

Leu Asp Ser Arg Gly Trp Gly Thr Leu Leu Ser Arg Ser Arg Ala Gly
 50                  55                  60

Leu Ala Gly Glu Ile Ala Gly Val Asn Trp Ser Gly Tyr Leu Val
 65                  70                  75                  80

Gly Ile Lys Arg Gln Arg Arg Leu Tyr Cys Asn Val Gly Ile Gly Phe
                 85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
```

```
                       165                 170                 175
Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
            195                 200                 205

<210> SEQ ID NO 16
<211> LENGTH: 194
<212> TYPE: PRT
<213> ORGANISM: Homo sapiens

<400> SEQUENCE: 16

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
        130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 17
<211> LENGTH: 233
<212> TYPE: PRT
<213> ORGANISM: Homo sapiens

<400> SEQUENCE: 17

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
                20                  25                  30

Gly Arg Glu Leu Ala Ser Leu Phe Arg Ala Gly Arg Glu Pro Gln Gly
            35                  40                  45

Val Ser Gln Gln His Val Arg Glu Gln Ser Leu Val Thr Asp Gln Leu
        50                  55                  60

Ser Arg Arg Leu Ile Arg Thr Tyr Gln Leu Tyr Ser Arg Thr Ser Gly
65                  70                  75                  80

Lys His Val Gln Val Leu Ala Asn Lys Arg Ile Asn Ala Met Ala Glu
                85                  90                  95
```

Asp Gly Asp Pro Phe Ala Lys Leu Ile Val Glu Thr Asp Thr Phe Gly
            100                 105                 110

Ser Arg Val Arg Val Arg Gly Ala Glu Thr Gly Leu Tyr Ile Cys Met
        115                 120                 125

Asn Lys Lys Gly Lys Leu Ile Ala Lys Ser Asn Gly Lys Gly Lys Asp
130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
            180                 185                 190

Met Lys Arg Leu Pro Arg Gly His His Thr Thr Glu Gln Ser Leu Arg
        195                 200                 205

Phe Glu Phe Leu Asn Tyr Pro Pro Phe Thr Arg Ser Leu Arg Gly Ser
    210                 215                 220

Gln Arg Thr Trp Ala Pro Glu Pro Arg
225                 230

<210> SEQ ID NO 18
<211> LENGTH: 208
<212> TYPE: PRT
<213> ORGANISM: Homo sapiens

<400> SEQUENCE: 18

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 19
<211> LENGTH: 208
<212> TYPE: PRT
<213> ORGANISM: Homo sapiens

<400> SEQUENCE: 19

| Met | Trp | Lys | Trp | Ile | Leu | Thr | His | Cys | Ala | Ser | Ala | Phe | Pro | His | Leu |
|---|---|---|---|---|---|---|---|---|---|---|---|---|---|---|---|
| 1 | | | | 5 | | | | | 10 | | | | | 15 | |

| Pro | Gly | Cys | Cys | Cys | Cys | Phe | Leu | Leu | Leu | Phe | Leu | Val | Ser | Ser |
|---|---|---|---|---|---|---|---|---|---|---|---|---|---|---|
| | | | 20 | | | | | 25 | | | | | 30 | |

| Val | Pro | Val | Thr | Cys | Gln | Ala | Leu | Gly | Gln | Asp | Met | Val | Ser | Pro | Glu |
|---|---|---|---|---|---|---|---|---|---|---|---|---|---|---|---|
| | | | 35 | | | | | 40 | | | | | 45 | | |

| Ala | Thr | Asn | Ser | Ser | Ser | Ser | Phe | Ser | Ser | Pro | Ser | Ser | Ala | Gly |
|---|---|---|---|---|---|---|---|---|---|---|---|---|---|---|
| | 50 | | | | | 55 | | | | | 60 | | | |

| Arg | His | Val | Arg | Ser | Tyr | Asn | His | Leu | Gln | Gly | Asp | Val | Arg | Trp | Arg |
|---|---|---|---|---|---|---|---|---|---|---|---|---|---|---|---|
| 65 | | | | | 70 | | | | | 75 | | | | | 80 |

| Lys | Leu | Phe | Ser | Phe | Thr | Lys | Tyr | Phe | Leu | Lys | Ile | Glu | Lys | Asn | Gly |
|---|---|---|---|---|---|---|---|---|---|---|---|---|---|---|---|
| | | | | 85 | | | | | 90 | | | | | 95 | |

| Lys | Val | Ser | Gly | Thr | Lys | Lys | Glu | Asn | Cys | Pro | Tyr | Ser | Ile | Leu | Glu |
|---|---|---|---|---|---|---|---|---|---|---|---|---|---|---|---|
| | | | 100 | | | | | 105 | | | | | 110 | | |

| Ile | Thr | Ser | Val | Glu | Ile | Gly | Val | Val | Ala | Val | Lys | Ala | Ile | Asn | Ser |
|---|---|---|---|---|---|---|---|---|---|---|---|---|---|---|---|
| | | 115 | | | | | 120 | | | | | 125 | | | |

| Asn | Tyr | Tyr | Leu | Ala | Met | Asn | Lys | Lys | Gly | Lys | Leu | Tyr | Gly | Ser | Lys |
|---|---|---|---|---|---|---|---|---|---|---|---|---|---|---|---|
| | 130 | | | | | 135 | | | | | 140 | | | | |

| Glu | Phe | Asn | Asn | Asp | Cys | Lys | Leu | Lys | Glu | Arg | Ile | Glu | Glu | Asn | Gly |
|---|---|---|---|---|---|---|---|---|---|---|---|---|---|---|---|
| 145 | | | | | 150 | | | | | 155 | | | | | 160 |

| Tyr | Asn | Thr | Tyr | Ala | Ser | Phe | Asn | Trp | Gln | His | Asn | Gly | Arg | Gln | Met |
|---|---|---|---|---|---|---|---|---|---|---|---|---|---|---|---|
| | | | | 165 | | | | | 170 | | | | | 175 | |

| Tyr | Val | Ala | Leu | Asn | Gly | Lys | Gly | Ala | Pro | Arg | Arg | Gly | Gln | Lys | Thr |
|---|---|---|---|---|---|---|---|---|---|---|---|---|---|---|---|
| | | | 180 | | | | | 185 | | | | | 190 | | |

| Arg | Arg | Lys | Asn | Thr | Ser | Ala | His | Phe | Leu | Pro | Met | Val | Val | His | Ser |
|---|---|---|---|---|---|---|---|---|---|---|---|---|---|---|---|
| | | 195 | | | | | 200 | | | | | 205 | | | |

<210> SEQ ID NO 20
<211> LENGTH: 225
<212> TYPE: PRT
<213> ORGANISM: Homo sapiens

<400> SEQUENCE: 20

| Met | Ala | Ala | Leu | Ala | Ser | Ser | Leu | Ile | Arg | Gln | Lys | Arg | Glu | Val | Arg |
|---|---|---|---|---|---|---|---|---|---|---|---|---|---|---|---|
| 1 | | | | 5 | | | | | 10 | | | | | 15 | |

| Glu | Pro | Gly | Gly | Ser | Arg | Pro | Val | Ser | Ala | Gln | Arg | Arg | Val | Cys | Pro |
|---|---|---|---|---|---|---|---|---|---|---|---|---|---|---|---|
| | | | 20 | | | | | 25 | | | | | 30 | | |

| Arg | Gly | Thr | Lys | Ser | Leu | Cys | Gln | Lys | Gln | Leu | Leu | Ile | Leu | Leu | Ser |
|---|---|---|---|---|---|---|---|---|---|---|---|---|---|---|---|
| | | | 35 | | | | | 40 | | | | | 45 | | |

| Lys | Val | Arg | Leu | Cys | Gly | Gly | Arg | Pro | Ala | Arg | Pro | Asp | Arg | Gly | Pro |
|---|---|---|---|---|---|---|---|---|---|---|---|---|---|---|---|
| | 50 | | | | | 55 | | | | | 60 | | | | |

| Glu | Pro | Gln | Leu | Lys | Gly | Ile | Val | Thr | Lys | Leu | Phe | Cys | Arg | Gln | Gly |
|---|---|---|---|---|---|---|---|---|---|---|---|---|---|---|---|
| 65 | | | | | 70 | | | | | 75 | | | | | 80 |

| Phe | Tyr | Leu | Gln | Ala | Asn | Pro | Asp | Gly | Ser | Ile | Gln | Gly | Thr | Pro | Glu |
|---|---|---|---|---|---|---|---|---|---|---|---|---|---|---|---|
| | | | | 85 | | | | | 90 | | | | | 95 | |

| Asp | Thr | Ser | Ser | Phe | Thr | His | Phe | Asn | Leu | Ile | Pro | Val | Gly | Leu | Arg |
|---|---|---|---|---|---|---|---|---|---|---|---|---|---|---|---|
| | | | 100 | | | | | 105 | | | | | 110 | | |

| Val | Val | Thr | Ile | Gln | Ser | Ala | Lys | Leu | Gly | His | Tyr | Met | Ala | Met | Asn |
|---|---|---|---|---|---|---|---|---|---|---|---|---|---|---|---|
| | | 115 | | | | | 120 | | | | | 125 | | | |

| Ala | Glu | Gly | Leu | Leu | Tyr | Ser | Ser | Pro | His | Phe | Thr | Ala | Glu | Cys | Arg |
|---|---|---|---|---|---|---|---|---|---|---|---|---|---|---|---|
| | 130 | | | | | 135 | | | | | 140 | | | | |

| Phe | Lys | Glu | Cys | Val | Phe | Glu | Asn | Tyr | Tyr | Val | Leu | Tyr | Ala | Ser | Ala |
|---|---|---|---|---|---|---|---|---|---|---|---|---|---|---|---|
| 145 | | | | | 150 | | | | | 155 | | | | | 160 |

| Leu | Tyr | Arg | Gln | Arg | Arg | Ser | Gly | Arg | Ala | Trp | Tyr | Leu | Gly | Leu | Asp |
|---|---|---|---|---|---|---|---|---|---|---|---|---|---|---|---|

```
                    165                 170                 175
Lys Glu Gly Gln Val Met Lys Gly Asn Arg Val Lys Lys Thr Lys Ala
            180                 185                 190

Ala Ala His Phe Leu Pro Lys Leu Leu Glu Val Ala Met Tyr Gln Glu
            195                 200                 205

Pro Ser Leu His Ser Val Pro Glu Ala Ser Pro Ser Ser Pro Pro Ala
            210                 215                 220

Pro
225

<210> SEQ ID NO 21
<211> LENGTH: 243
<212> TYPE: PRT
<213> ORGANISM: Homo sapiens

<400> SEQUENCE: 21

Met Ala Ala Ala Ile Ala Ser Ser Leu Ile Arg Gln Lys Arg Gln Ala
1               5                   10                  15

Arg Glu Ser Asn Ser Asp Arg Val Ser Ala Ser Lys Arg Arg Ser Ser
            20                  25                  30

Pro Ser Lys Asp Gly Arg Ser Leu Cys Glu Arg His Val Leu Gly Val
        35                  40                  45

Phe Ser Lys Val Arg Phe Cys Ser Gly Arg Lys Arg Pro Val Arg Arg
    50                  55                  60

Arg Pro Glu Pro Gln Leu Lys Gly Ile Val Thr Arg Leu Phe Ser Gln
65                  70                  75                  80

Gln Gly Tyr Phe Leu Gln Met His Pro Asp Gly Thr Ile Asp Gly Thr
                85                  90                  95

Lys Asp Glu Asn Ser Asp Tyr Thr Leu Phe Asn Leu Ile Pro Val Gly
            100                 105                 110

Leu Arg Val Val Ala Ile Gln Gly Val Lys Ala Ser Leu Tyr Val Ala
        115                 120                 125

Met Asn Gly Glu Gly Tyr Leu Tyr Ser Ser Asp Val Phe Thr Pro Glu
    130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Thr
            180                 185                 190

Lys Pro Ser Ser His Phe Val Pro Lys Pro Ile Glu Val Cys Met Tyr
        195                 200                 205

Arg Glu Pro Ser Leu His Glu Ile Gly Glu Lys Gln Gly Arg Ser Arg
    210                 215                 220

Lys Ser Ser Gly Thr Pro Thr Met Asn Gly Gly Lys Val Val Asn Gln
225                 230                 235                 240

Asp Ser Thr

<210> SEQ ID NO 22
<211> LENGTH: 245
<212> TYPE: PRT
<213> ORGANISM: Homo sapiens

<400> SEQUENCE: 22

Met Ala Ala Ala Ile Ala Ser Ser Leu Ile Arg Gln Lys Arg Gln Ala
1               5                   10                  15
```

```
Arg Glu Arg Glu Lys Ser Asn Ala Cys Lys Cys Val Ser Ser Pro Ser
            20                  25                  30

Lys Gly Lys Thr Ser Cys Asp Lys Asn Lys Leu Asn Val Phe Ser Arg
        35                  40                  45

Val Lys Leu Phe Gly Ser Lys Lys Arg Arg Arg Arg Pro Glu Pro
 50                  55                  60

Gln Leu Lys Gly Ile Val Thr Lys Leu Tyr Ser Arg Gln Gly Tyr His
 65                  70                  75                  80

Leu Gln Leu Gln Ala Asp Gly Thr Ile Asp Gly Thr Lys Asp Glu Asp
                85                  90                  95

Ser Thr Tyr Thr Leu Phe Asn Leu Ile Pro Val Gly Leu Arg Val Val
                100                 105                 110

Ala Ile Gln Gly Val Gln Thr Lys Leu Tyr Leu Ala Met Asn Ser Glu
                115                 120                 125

Gly Tyr Leu Tyr Thr Ser Glu Leu Phe Thr Pro Glu Cys Lys Phe Lys
                130                 135                 140

Glu Ser Val Phe Glu Asn Tyr Tyr Val Thr Tyr Ser Ser Met Ile Tyr
145                 150                 155                 160

Arg Gln Gln Gln Ser Gly Arg Gly Trp Tyr Leu Gly Leu Asn Lys Glu
                165                 170                 175

Gly Glu Ile Met Lys Gly Asn His Val Lys Lys Asn Lys Pro Ala Ala
                180                 185                 190

His Phe Leu Pro Lys Pro Leu Lys Val Ala Met Tyr Lys Glu Pro Ser
                195                 200                 205

Leu His Asp Leu Thr Glu Phe Ser Arg Ser Gly Ser Gly Thr Pro Thr
                210                 215                 220

Lys Ser Arg Ser Val Ser Gly Val Leu Asn Gly Gly Lys Ser Met Ser
225                 230                 235                 240

His Asn Glu Ser Thr
                245

<210> SEQ ID NO 23
<211> LENGTH: 247
<212> TYPE: PRT
<213> ORGANISM: Homo sapiens

<400> SEQUENCE: 23

Met Ala Ala Ile Ala Ser Gly Leu Ile Arg Gln Lys Arg Gln Ala
 1               5                  10                  15

Arg Glu Gln His Trp Asp Arg Pro Ser Ala Ser Arg Arg Arg Ser Ser
            20                  25                  30

Pro Ser Lys Asn Arg Gly Leu Cys Asn Gly Asn Leu Val Asp Ile Phe
        35                  40                  45

Ser Lys Val Arg Ile Phe Gly Leu Lys Lys Arg Arg Leu Arg Gln
 50                  55                  60

Asp Pro Gln Leu Lys Gly Ile Val Thr Arg Leu Tyr Cys Arg Gln Gly
 65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
                100                 105                 110

Val Val Ala Ile Gln Gly Val Lys Thr Gly Leu Tyr Ile Ala Met Asn
                115                 120                 125

Gly Glu Gly Tyr Leu Tyr Pro Ser Glu Leu Phe Thr Pro Glu Cys Lys
                130                 135                 140
```

Phe Lys Glu Ser Val Phe Glu Asn Tyr Tyr Val Ile Tyr Ser Ser Met
145                 150                 155                 160

Leu Tyr Arg Gln Gln Ser Gly Arg Ala Trp Phe Leu Gly Leu Asn
            165                 170                 175

Lys Glu Gly Gln Ala Met Lys Gly Asn Arg Val Lys Thr Lys Pro
            180                 185                 190

Ala Ala His Phe Leu Pro Lys Pro Leu Glu Val Ala Met Tyr Arg Glu
            195                 200                 205

Pro Ser Leu His Asp Val Gly Glu Thr Val Pro Lys Pro Gly Val Thr
210                 215                 220

Pro Ser Lys Ser Thr Ser Ala Ser Ala Ile Met Asn Gly Gly Lys Pro
225                 230                 235                 240

Val Asn Lys Ser Lys Thr Thr
            245

<210> SEQ ID NO 24
<211> LENGTH: 218
<212> TYPE: PRT
<213> ORGANISM: Mus musculus

<400> SEQUENCE: 24

Met Ala Arg Lys Trp Asn Gly Arg Ala Val Arg Ala Leu Val Leu
1               5                   10                  15

Ala Thr Leu Trp Leu Ala Val Ser Gly Arg Pro Leu Ala Gln Gln Ser
            20                  25                  30

Gln Ser Val Ser Asp Glu Asp Pro Leu Phe Leu Tyr Gly Trp Gly Lys
        35                  40                  45

Ile Thr Arg Leu Gln Tyr Leu Tyr Ser Ala Gly Pro Tyr Val Ser Asn
50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
            85                  90                  95

Ile Ala Ile Lys Asp Val Ser Val Arg Tyr Leu Cys Met Ser Ala
            100                 105                 110

Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
            165                 170                 175

Phe Phe Glu Thr Gly Asp Gln Leu Arg Ser Lys Met Phe Ser Leu Pro
        180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
210                 215

<210> SEQ ID NO 25
<211> LENGTH: 207
<212> TYPE: PRT
<213> ORGANISM: Homo sapiens

<400> SEQUENCE: 25

Met Ala Glu Val Gly Gly Val Phe Ala Ser Leu Asp Trp Asp Leu His

```
            1               5                  10                 15
Gly Phe Ser Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
            35                  40                  45

Ser Pro Thr Asp Phe Ala His Leu Lys Gly Ile Leu Arg Arg Arg Gln
        50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
        195                 200                 205
```

<210> SEQ ID NO 26
<211> LENGTH: 216
<212> TYPE: PRT
<213> ORGANISM: Homo sapiens

<400> SEQUENCE: 26

```
Met Gly Ala Ala Arg Leu Leu Pro Asn Leu Thr Leu Cys Leu Gln Leu
1               5                   10                  15

Leu Ile Leu Cys Cys Gln Thr Gln Gly Glu Asn His Pro Ser Pro Asn
                20                  25                  30

Phe Asn Gln Tyr Val Arg Asp Gln Gly Ala Met Thr Asp Gln Leu Ser
            35                  40                  45

Arg Arg Gln Ile Arg Glu Tyr Gln Leu Tyr Ser Arg Thr Ser Gly Lys
        50                  55                  60

His Val Gln Val Thr Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
            100                 105                 110

Arg Gly Lys Leu Ile Gly Lys Pro Ser Gly Lys Ser Lys Asp Cys Val
        115                 120                 125

Phe Thr Glu Ile Val Leu Glu Asn Asn Tyr Thr Ala Phe Gln Asn Ala
130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
```

```
            180                 185                 190
Lys Gln Phe Glu Phe Val Gly Ser Ala Pro Thr Arg Arg Thr Lys Arg
        195                 200                 205

Thr Arg Arg Pro Gln Pro Leu Thr
    210                 215

<210> SEQ ID NO 27
<211> LENGTH: 207
<212> TYPE: PRT
<213> ORGANISM: Homo sapiens

<400> SEQUENCE: 27

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 28
<211> LENGTH: 216
<212> TYPE: PRT
<213> ORGANISM: Homo sapiens

<400> SEQUENCE: 28

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95
```

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
        180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 29
<211> LENGTH: 211
<212> TYPE: PRT
<213> ORGANISM: Homo sapiens

<400> SEQUENCE: 29

Met Ala Pro Leu Ala Glu Val Gly Phe Leu Gly Gly Leu Glu Gly
1               5                   10                  15

Leu Gly Gln Gln Val Gly Ser His Phe Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
        180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 30
<211> LENGTH: 209
<212> TYPE: PRT
<213> ORGANISM: Homo sapiens

<400> SEQUENCE: 30

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 31
<211> LENGTH: 170
<212> TYPE: PRT
<213> ORGANISM: Homo sapiens

<400> SEQUENCE: 31

```
Met Arg Arg Arg Leu Trp Leu Gly Leu Ala Trp Leu Leu Leu Ala Arg
1               5                   10                  15

Ala Pro Asp Ala Ala Gly Thr Pro Ser Ala Ser Arg Gly Pro Arg Ser
            20                  25                  30

Tyr Pro His Leu Glu Gly Asp Val Arg Trp Arg Arg Leu Phe Ser Ser
        35                  40                  45

Thr His Phe Phe Leu Arg Val Asp Pro Gly Gly Arg Val Gln Gly Thr
    50                  55                  60

Arg Trp Arg His Gly Gln Asp Ser Ile Leu Glu Ile Arg Ser Val His
65                  70                  75                  80

Val Gly Val Val Val Ile Lys Ala Val Ser Ser Gly Phe Tyr Val Ala
                85                  90                  95

Met Asn Arg Arg Gly Arg Leu Tyr Gly Ser Arg Leu Tyr Thr Val Asp
            100                 105                 110

Cys Arg Phe Arg Glu Arg Ile Glu Glu Asn Gly His Asn Thr Tyr Ala
        115                 120                 125

Ser Gln Arg Trp Arg Arg Gly Gln Pro Met Phe Leu Ala Leu Asp
        130                 135                 140

Arg Arg Gly Gly Pro Arg Pro Gly Gly Arg Thr Arg Arg Tyr His Leu
```

-continued

```
                145                 150                 155                 160
Ser Ala His Phe Leu Pro Val Leu Val Ser
                    165                 170

<210> SEQ ID NO 32
<211> LENGTH: 251
<212> TYPE: PRT
<213> ORGANISM: Homo sapiens

<400> SEQUENCE: 32

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
                35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```